Figure 1:
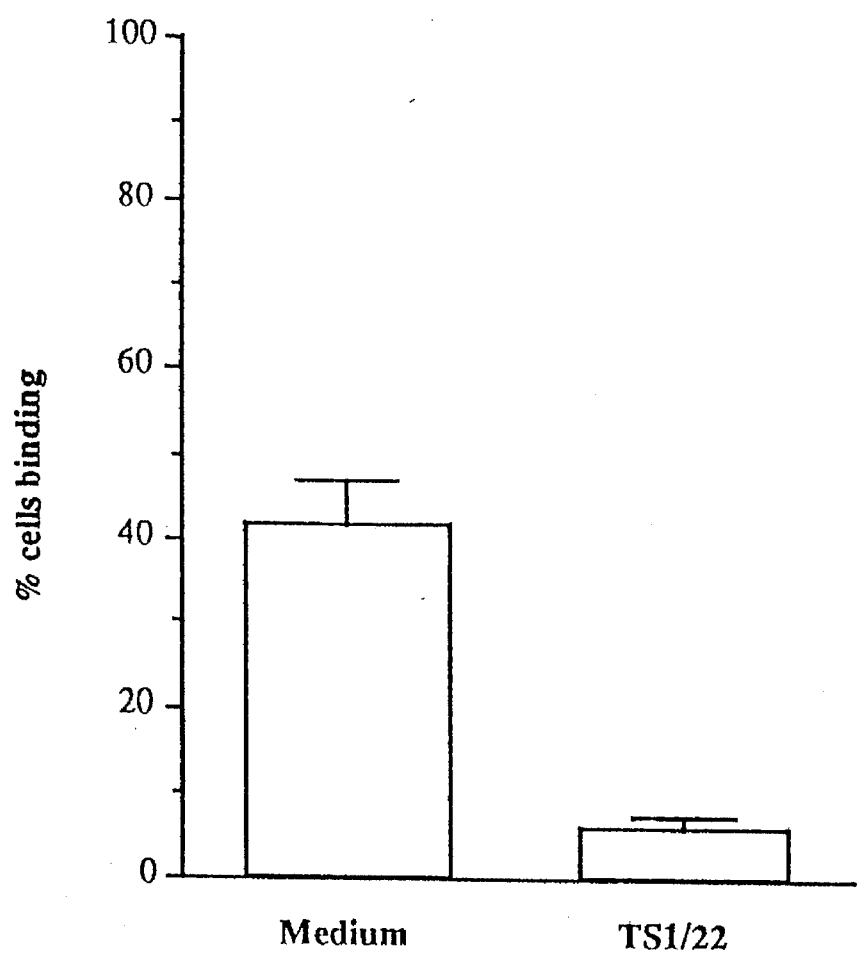

United States Patent [19]

Vonderheide et al.

[11] Patent Number: 5,599,676

[45] Date of Patent: Feb. 4, 1997

[54] METHOD FOR ISOLATING A NOVEL RECEPTOR FOR α4 INTEGRINS

[75] Inventors: Robert H. Vonderheide, Brookline; Timothy A. Springer, Chestnut Hill, both of Mass.

[73] Assignee: Center for Blood Research, Inc., Boston, Mass.

[21] Appl. No.: 323,199

[22] Filed: Oct. 14, 1994

Related U.S. Application Data

[63] Continuation of Ser. No. 886,992, May 21, 1992, abandoned.

[51] Int. Cl.$^6$ .................. C12Q 1/02; C12N 15/12; C07K 16/00
[52] U.S. Cl. ............ 435/7.2; 435/69.1; 435/252.3; 435/252.33; 435/254.11; 435/320.1; 435/91.1; 536/23.1; 530/387.1; 935/79
[58] Field of Search .................. 435/69.1, 240.1, 435/240.2, 252.3, 252.33, 254.11, 320.1, 7.2, 7.21; 536/23.1; 530/387.1; 935/79

[56] References Cited

PUBLICATIONS

Aruffo and Seed, 1987, "Molecular cloning of a CD28 cDNA by a high-efficiency COS cell expression system," Proc. Natl. Acad. Sci. USA 84:8573–8577.
Mizushima and Nagata, 1990, "pEF–BOS, a powerful mammalian expression vector," Nucl. Acids Res. 18(17):5322.
Sambrook and Gething, 1988, "Vectors for high level expression of proteins in mammalian cells," Focus 10(3):41–48.
Sambrook et al., 1989, Molecular Cloning, A Laboratory Manual, 2d ed., Cold Spring Harbor Laboratory Press, New York, pp. 16.17–16.22, 16.69, and 16.73–16.81.
Seed, 1987, "An LFA–3 cDNA encodes a phospholopid–linked membrane protein homologous to its receptor CD2," Nature 329:840–842.
Seed and Aruffo, 1987, "Molecular cloning of the CD2 antigen, the T–cell erythrocyte receptor, by a rapid immunoselection procedure," Proc. Natl. Acad. Sci. USA 84:3365–3369.
Simmons and Seed, 1988, "Isolation of a cDNA encoding CD33, a differentiation antigen of myeloid progenitor cells," J. Immunol. 141:2797–2800.
Wong et al., 1985, "Human GM–CSF: molecular cloning of the complementary DNA and purification of the natural and recombinant proteins," Science 228:810–815.
Yang et al., 1986, "Human IL–3 (multi–CSF): identification by expression cloning of a novel hematopoietic growth factor related to murine IL–3," Cell 47:3–10.
Chan, et al., 1992, Adhesion to vascular cell adhesion molecule 1 and fibronectin comparison of $\alpha^4\beta_1$ (VLA–4) and $\alpha^4\beta_7$ on the human B cell line JY, J. Biol. Chem. 267:8366–8370.
Hemler, et al., 1987, Characterization of the cell surface heterodimer VLA–4 and related peptides, J. Biol. Chem. 262:11478–11485.

Elices, et al., 1990, VCAM–1 on activated endothelium interacts with the leukocyte integrin VLA–4 at a site distinct from the VLA–4/fibronectin binding site, Cell 60:577–584.
Shimizu, et al., 1990, Regulated expression and binding of three VLA (β1) integrin receptors on T cells, Nature 345:250–253.
Chan, et al., 1992, Distinct cellular functions mediated by different VLA integrin α subunit cytoplasmic domains, Cell 68:1051–1060.
Staunton, et al., 1989, Functional cloning of ICAM–2, a cell adhesion ligand of LFA–1 homologous to ICAM–1, Nature 339:61–64.
de Fougerolles, et al., 1991, Characterization of ICAM–2 and evidence for a third counter–receptor fo LFA–1, J. Exp. Med. 174:253–267.
de Fougerolles and Springer, 1992, Intercellular adhesion molecule 3, a third adhesion counter receptor for lymphocyte function–associated molecule 1 on resting lymphocytes, J. Exp. Med. 175:185–190.
Springer, 1990, Adhesion receptors of the immune system, Nature 346:425–433.
Pober and Cotran, 1990, The role of endothelial cells in inflammation, Transplantation 50:537–544.
Dustin and Springer, 1988, Lumphocyte function–associated antigen–1 (LFA–1) interaction with intercellular adhesion molecule–1 (ICAM–1) is one of at least three mechanisms for lymphocyte adhesion to cultured endothelial cells, J. Cell. Biol. 107:312–331.
Schwartz et al., 1990, Identification of surface proteins mediating adherence of CD11/CD18–deficient lymphoblastoid cells to cultured human endothelium. J. Clin. Invest. 85:2019–2022.
Pober et al., 1986, Overlapping patterns of activation of human endothelial cells by interleukin 1, tumor necrosis factor, and immune interferon. J. Immunol. 137(6): 1893–1896.
Kishimoto et al., 1989, The leukocyte integrins, Adv. Immunol. 46:149–182.
Springer et al., 1987, The lymphocyte function–associated LFA–1, CD2, and LFA–3 molecules: Cell adhesion receptors of the Immune System, Ann. Rev. Immunol. 5:223–252.
Carlos et al., 1990, Membrane proteins involved in phagocyte adherence to endothelium, Immunol. Rev. 114:5–28.

(List continued on next page.)

Primary Examiner—Stephen G. Walsh
Assistant Examiner—Sally P. Teng
Attorney, Agent, or Firm—Pennie & Edmonds

[57] ABSTRACT

The present invention is directed to a method for isolating a novel receptor for α4 integrins such as VLA-4, that is distinct from VCAM-1 and from fibronectin. Isolated nucleic acids encoding the receptor and antibodies to the receptor are also provided. The invention is also directed to pharmaceutical compositions, and methods of treating disorders involving an undesirable inflammatory or immune response by administering the VLA-4 receptor of the invention.

10 Claims, 7 Drawing Sheets

PUBLICATIONS

Osborn et al., 1989 Direct expression cloning of vascular cell adhesion molecule 1, a cytokine–induced endothelial protein that binds to lymphocytes, Cell 59:1203–1211.

Wellicome et al., 1990, A monoclonal antibody that detects a novel antigen on endothelial cells that is induced by tumor necrosis factor, IL–1, or lipopolysaccharide, J. Immunol. 144:2558–2565.

Rice et al., 1990, Inducible cell adhesion molecule 110 (INCAM–110) is an endothelial receptor for lymphocytes, J. Exp. Med. 171:1369–1374.

Carlos, et al. 1990, Vascular cell adhesion molecule–1 mediates lymphocyte adherence to cytokine–activated cultured human endothelial cells, Blood 76:965–970.

Guan and Hynes, 1990, Lymphoid cells recognize alternatively spliced segment of fibronectin via the integrin receptor $\alpha_4\beta_1$, Cell 60:53–61.

Wayner et al., 1989 Identification and characterization of the T lymphocyte adhesion receptor for an alternative cell attachment domain (CS–1) in plasma fibronectin, J. Cell Biol. 109:1321–1330.

Hemler, 1990, VLA proteins in the integrin family: structures, functions, and their role on leukocytes, Ann. Rev. Immunol 8:365–400.

Clayberger et al., 1987, Identification and characterization of two novel lymphocyte function–associated antigens L24 and L25. J. Immunol. 138(5):1510–1514.

Miyake et al., 1991, Evidence for a role of the Integrin VLA–4 in lympho–hemopoiesis. J. Exp. Med. 173:599–607.

Williams et al., 1991, Fibronectin and VLA–4 in haematopoietic stem cell–microenvironment interactions. Nature 352:438–441.

Miyake et al., 1991, A VCAM–like adhesion molecule on murine bone marrow stromal cell mediates binding of lymphocyte precursors in culture. J. Cell. Biol. 114(3):557–565.

Ryan et al., 1991, Vascular cell adhesion molecule–1 and the integrin VLA–4 mediate adhesion of human B cell precursors to cultured bone marrow adherent cells, J. Clin. Invest 88:995–1004.

Freeman et al., 1990, Adhesion of human B cells to germinal centers in vitro involves VLA–4 and INCAM–110. Science 249:1030–1033.

Taichman et al., 1991, Tumor cell surface $\alpha^4\beta_1$ integrin mediates adhesion to vascular endothelium: demonstration of an interaction with the N–terminal domains of INCAM–110/VCAM–1. Cell. Reg. 2:347–355.

Rice and Bevilacqua, 1989, An inducible endothelial cell surface glycoprotein mediates melanoma adhesion. Science 246:1303–1306.

Cybulsky and Gimbrone, 1991, Endothelial expression of a mononuclear leukocyte adhesion molecule during antherogenesis. Science 251:788–791.

Briscoe et al., 1991, Induced expression of endothelial–leukocyte adhesion molecules in human cardiac allografts, Transplantation 51:537–547.

Cybulsky et al., 1991, Gene structure, chromosomal location, and basis for alternative mRNA splicing of the human $VCAM_1$ gene. Proc. Natl. Acad. Sci. USA. 88:7859–7863.

Polte et al., 1990, Full length vascular cell adhesion molecule 1 (VCAM–1), Nucl. Acids. Res. 18:5901.

Cybulsky et al., 1991, Alternative splicing of human VCAM–1 in activated vascular endothelium, Amer. J. of Path. 138:815–820.

Hession et al., 1991, Cloning of an alternate form of vascular cell adhesion molecule–1 (VCAM1), J. Biol. Chem. 266:6682–6685.

Rothlein et al., 1986, A human intercellular adhesion molecule (ICAM–1) distinct from LFA–1. J. Immunol 137(4): 1270–1274.

Makgoba et al., 1988, Functional evidence that intercellular adhesion molecule–1 (ICAM–1) is a ligand for LFA–1–dependent adhesion in T cell–mediated cytotoxicity, Eur. J. Immunol 18:637–640.

Oppenheimer–Marks et al., 1991, Differential utilization of ICAM–1 and VCAM–1 during the adhesion and transendothelial migration of human T lymphocytes, J. Immunol 147(9):2913–2921.

Anderson and Springer, 1987, Leukocyte adhesion deficiency: an inherited defet in the Mac–1, LFA–1, and p 150,95 glycoproteins, Ann. Rev. Med. 38:175–194.

Graber et al., 1990, T cells bind to cytokine–activated endothelial cells via a novel, inducible sialoglycoprotein and endothelial leukocyte adhesion molecule–1. J. Immunol 145(3):819–830.

Thornhill et al., 1991, Tumor necrosis factor combines with IL–4 or IFN–y to selectively enhance endothelial cell adhesiveness for T cells. The contribution of vascular cell adhesion molecule–1–dependent and independent binding mechanisms. J. Immunol 146(2):592–598.

Pulido et al., 1991, Functional evidence for three distinct and independently inhibitable adhesion activities mediated by the human integrin VLA–4. J. Biol. Chem. 266(16):10241–10245.

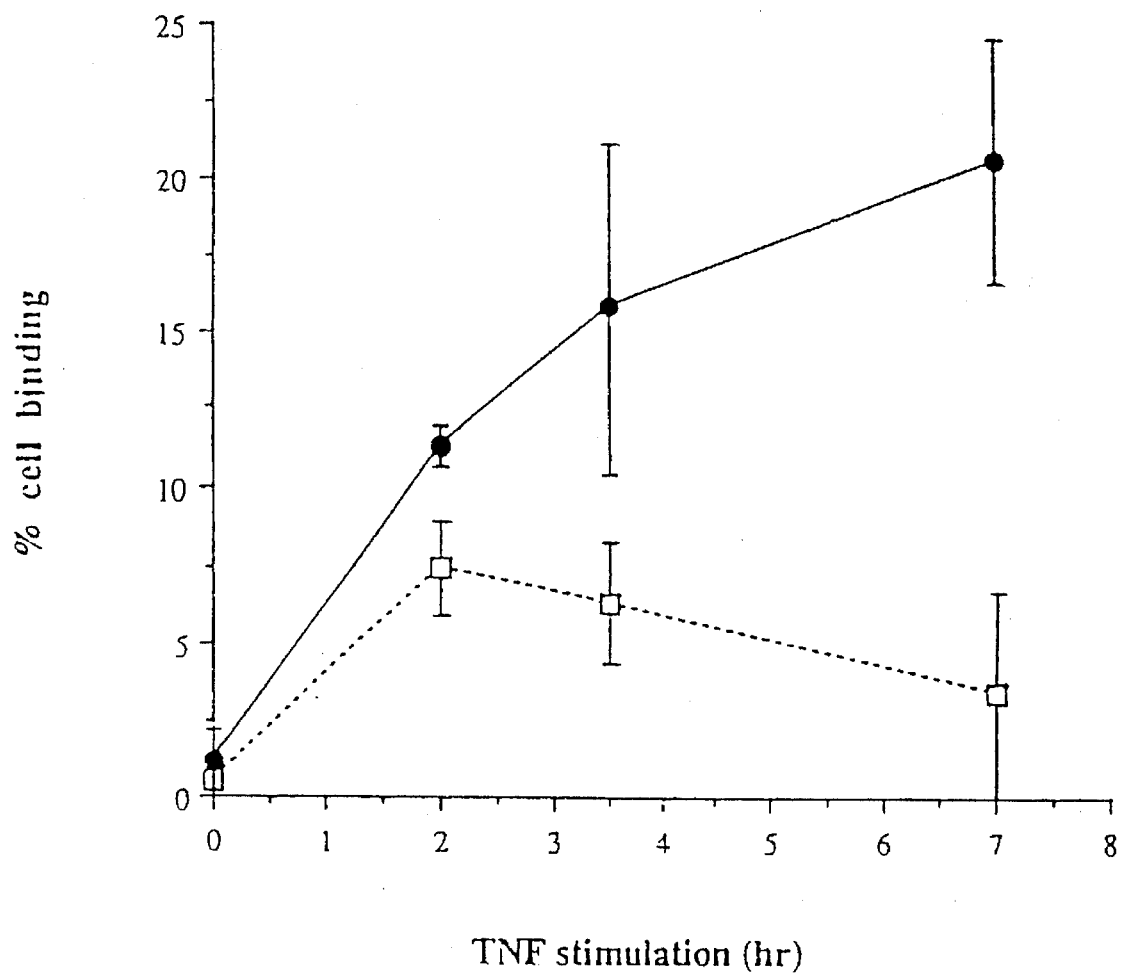

METHOD FOR ISOLATING A NOVEL RECEPTOR FOR α4 INTEGRINS

This invention was made with government support under grant number CA-31798 awarded by the National Institutes of Health. The government has certain rights in the invention.

This is a continuation of application Ser. No. 07/886,992, filed May 21, 1992, now abandoned.

TABLE OF CONTENTS

1. INTRODUCTION
2. BACKGROUND OF THE INVENTION
3. SUMMARY OF THE INVENTION
   3.1. DEFINITIONS
4. DESCRIPTION OF THE FIGURES
5. DETAILED DESCRIPTION OF THE INVENTION
   5.1. ISOLATION OF THE α4 INTEGRIN RECEPTOR GENE
   5.2. RECOMBINANT EXPRESSION OF THE α4 INTEGRIN RECEPTOR
   5.3. PURIFICATION OF THE α4 INTEGRIN RECEPTOR
   5.4. STRUCTURE OF THE RECEPTOR GENE AND PROTEIN
      5.4.1. GENETIC ANALYSIS
      5.4.2. PROTEIN ANALYSIS
   5.5. DERIVATIVES AND ANALOGS OF THE RECEPTOR
   5.6. ASSAYS OF RECEPTOR PROTEINS, DERIVATIVES AND ANALOGS
   5.7. GENERATION AND USE OF ANTIBODIES TO THE α4 INTEGRIN RECEPTOR
      5.7.1. ASSAYS FOR NEUTRALIZING ANTIBODIES
   5.8. IDENTIFICATION OF INHIBITORS OF THE BINDING OF AN α4 INTEGRIN TO THE α4 INTEGRIN RECEPTOR
   5.9. THERAPEUTIC USES OF THE α4 INTEGRIN RECEPTOR, ANTIBODIES THERETO, AND α4 INHIBITORS
      5.9.1. DEMONSTRATION OF THERAPEUTIC UTILITY
      5.9.2. THERAPEUTIC ADMINISTRATION AND COMPOSITIONS
6. LYMPHOCYTE ADHESION THROUGH VLA-4: EVIDENCE FOR AN ADDITIONAL α4 INTEGRIN COUNTER-RECEPTOR ON STIMULATED ENDOTHELIUM
   6.1. MATERIALS AND METHODS
      6.1.1. CELL CULTURE
      6.1.2. ANTIBODIES
      6.1.3. HUVEC ADHESION ASSAY
      6.1.4. FIBRONECTIN ADHESION ASSAY
   6.2. RESULTS
      6.2.1. VLA-4-DEPENDENT ADHESION OF LYMPHOCYTIC CELL LINES TO TNF-STIMULATED AND UNSTIMULATED HUVEC
      6.2.2. A LIGAND ON STIMULATED ENDOTHELIUM DISTINCT FROM VCAM-1 AND FIBRONECTIN
      6.2.3. INDUCTION OF E1/6-DEPENDENT/VLA-4-DEPENDENT RAMOS CELL ADHESION TO TNF-STIMULATED HUVEC
   6.3. DISCUSSION
7. FUNCTIONAL CLONING OF THE VLA-4 RECEPTOR
   7.1. PANNING METHOD
   7.2. ROSETTE METHOD
   7.3. SUBPOOL SELECTION
8. PRODUCTION OF ANTIBODY AND ISOLATION OF THE α4 RECEPTOR BY ANTIBODY BINDING

1. INTRODUCTION

The present invention relates to a receptor for α4 integrins such as VLA-4, that is distinct from VCAM-1 and fibronectin, and therapeutic uses of such receptor.

2. BACKGROUND OF THE INVENTION

Molecular interactions between the surfaces of lymphocytes and endothelial cells play a critical role in the extravasation (migration into tissue) of lymphocytes from the blood stream (Springer, 1990, Nature 346:425; Pober and Cotran, 1990, Transplantation 50:537). Studies from this (Dustin and Springer, 1988, J. Cell Biol. 107:321; de Fougerolles et al., 1991, J. Exp. Med. 174:253) and other laboratories (Elices et al., 1990, Cell 60:577; Schwartz et al., 1990, J. Clin. Invest. 85:2019) demonstrate that two members of the integrin family of cell-surface heterodimers—lymphocyte function-associated antigen-1 (LFA-1) and very late activation antigen-4 (VLA-4)—mediate distinct mechanisms for lymphocyte-endothelial cell adhesion. LFA-1, whose expression is limited to leukocytes, can bind to intercellular adhesion molecule-1 (ICAM-1) or to ICAM-2 on the surface of stimulated or unstimulated endothelial cells (Springer, 1990, Nature 346:425). ICAM-1 expression by endothelial cells in culture is substantially upregulated following stimulation by pro-inflammatory cytokines such as TNF, IL-1, or INF-γ (Dustin and Springer, 1988, J. Cell Biol. 107:321; Pober et al., 1986, J. Immunol. 137:1893). ICAM-2 expression is constitutively high in vitro and not upregulated by cytokines (de Fougerolles et al., 1991, J. Exp. Med. 174:253; Staunton et al., 1989., Nature 339:61). ICAM-1 and ICAM-2 are also constitutively expressed by peripheral blood lymphocytes, with ICAM-1 showing a significant increase in expression following cell activation (de Fougerolles et al., 1991, J. Exp. Med. 174:253). Interactions between LFA-1 and its counter-receptors have been implicated in a number of lymphocyte functions, including cytotoxic T lymphocyte killing, delivery of T cell help, B lymphocyte responses, and graft rejection, as well as the adherence of lymphocytes and neutrophils to endothelial cells, fibroblasts, or epithelial cells (Springer, 1990, Nature 346:425; Kishimoto et al., 1989, Adv. Immunol. 46:149; Springer et al., 1987, Annu. Rev. Immunol. 5:223; Carlos and Harlan, 1990, Immunol. Rev. 114:1).

The integrin VLA-4, that contains the α4 (CD49d) subunit noncovalently associated with the β1 (CD29) subunit, is expressed by lymphocytes, monocytes, and neural crest-derived cells, and can interact with vascular cell adhesion molecule-1 (VCAM-1) (Elices et al., 1990, Cell 60:577). Like ICAM-1 and ICAM-2, VCAM-1 is a member of the immunoglobulin (Ig) superfamily (Osborn et al., 1989, Cell 59:1203), but unlike the ICAMs, VCAM-1 is not expressed by lymphocytes (Wellicome et al., 1990, J. Immunol. 144:2558; Rice et al., 1990, J. Exp. Med. 171:1369). VCAM-1 expression is very low or absent on resting endothelial cells in culture but can be induced by cytokines such as TNF or IL-1 with kinetics of induction similar but not identical to that of ICAM-1 (Wellicome et al., 1990, J. Immunol. 144:2558; Carlos et al., 1990, Blood 76:965). Peak expression of VCAM-1 after continuous treatment of endothelial cells with TNF in culture occurs somewhat earlier than the peak expression of ICAM-1, but both persist at levels substantially higher than basal expression for at least 48 hr (Carlos et al., 1990, Blood 76:965). Unlike LFA-1, however, VLA-4 can also interact with fibronectin, binding to the alternatively spliced CS-1 region located C-terminal to the RGD site of fibronectin recognized by the integrin VLA-5 (Guan and Hynes, 1990, Cell 60:53; Wayner et al., 1989, J. Cell Biol. 109:1321; Hemler, 1990, Annu. Rev. Immunol. 8:365). VLA-4 and its counter-receptors have been implicated in a number of physiologic and pathophysiologic processes in addition to lymphocyte-endothelial cell adhesion including cytotoxic T cell killing (Clayberger et al., 1987, J. Immunol. 138:1510), lymphopoiesis (Miyake et al., 1991, J. Exp. Med. 173:599; Williams et al., 1991, Nature 352:438; Miyake et al., 1991, J. Cell Biol. 114:557; Ryan et al., 1991, J. Clin. Invest. 88:995), germinal center development (Freedman et al., 1990, Science 249:1030), tumor metastasis (Taichman et al., 1991, Cell Regul. 2:347; Rice and Bevilacqua, 1989, Science 246:1303), atherogenesis (Cybulsky and Gimbrone, 1991, Science 251:788), and acute graft rejection (Briscoe et al., 1991, Transplantation 51:537).

Recent studies have demonstrated that two different VCAM-1 precursors can be produced by alternative mRNA splicing (Cybulsky et al., 1991, Proc. Natl. Acad. Sci. U.S.A. 88:7859; Polte et al., 1990, Nucleic Acids Res. 18:5901; Cybulsky et al., 1991, Am. J. Pathol. 138:815; Hession et al., 1991, J. Biol. Chem. 266:6682). The original VCAM-1 cDNA clone encodes a transmembrane glycoprotein with six predicted immunoglobulin-like domains (VCAM-6D) (Osborn et al., 1989, Cell 59:1203). Several subsequently identified VCAM-1 cDNA clones, which were produced from stimulated HUVEC using polymerase chain reaction, differ from the original clone by containing a 276 base-pair insert predicted to encode an additional immunoglobulin-like domain after the first three domains of VCAM-1, suggesting a seven-domain form of VCAM-1 (VCAM-7D) (Polte et al., 1990, Nucl. Acids Res. 18:5901; Cybulsky et al., 1991, Am. J. Pathol. 138:815; Hession et al., 1991, J. Biol. Chem. 266:6682). The two forms of VCAM-1 MRNA most likely represent alternatively spliced products of the same precursor MRNA.

There is increasing evidence for multiple ligand recognition by integrins. A strategy comparing the inhibitory effects of receptor and counter-receptor monoclonal antibody (mAb) was used to provide evidence for LFA-1 counter-receptors distinct from ICAM-1 (Dustin et al., 1988, J. Cell. Biol. 107–321; Rothlein et al., 1986, J. Immunol. 137:1270; Makgoba et al., 1988, Eur. J. Immunol. 18:637), and led to the subsequent identification of ICAM-2 and ICAM-3 (de Fougerolles and Springer, 1991, J. Exp. Med. 174:253; Staunton et al., 1989, Nature 339:61; de Fougerolles and Springer, 1991, J. Exp. Med. In press). Although VLA-4 has been shown to bind to fibronectin and VCAM-1, it has not been known whether VLA-4 interacts with other ligand(s) completely distinct from VCAM-1.

Adhesion to endothelium that is dependent on α4 integrin(s) and that is not ascribable to VCAM-1 or fibronectin has not been suggested by the prior art. One previous study of resting T cell adhesion to stimulated HUVEC found no difference in inhibition between the anti-VCAM-1 mAb 4β9 and a function-blocking anti-VLA-4 mAb (Oppenheimer-Marks et al., 1991, J. Immunol. 147:2913). In a study (Schwartz et al., 1990, J. Clin. Invest. 85:2019) of LFA-1-negative B cells obtained from a patient with leukocyte adhesion deficiency (Anderson and Springer, 1987, Annu. Rev. Med. 38:175), mAb 4B9 failed to inhibit binding to stimulated HUVEC as well as a function-blocking anti-VLA-4 mAb; the difference was attributed to lymphocyte interactions with fibronectin on HUVEC. In studies (Graber et al., 1990, J. Immunol. 145:819; Thornhill et al., 1991, J. Immunol. 146:592) of other anti-VCAM-1 mAb used with various mAbs that block LFA-1 function, binding of resting T cells to stimulated HUVEC was found to be inhibited but not to the same level as binding to unstimulated HUVEC in the presence of the same mAbs. In one study of a lymphocytic cell line (Pulido et al., 1991, J. Biol Chem. 266:10241), mAb 4B9 and HP2/1 inhibited binding to stimulated HUVEC equally well. In another study of cell lines (Carlos et al., 1990, Blood 76:965), however, binding to stimulated HUVEC after preincubation with 4B9 and a mAb to LFA-1 β chain was greater than binding to unstimulated HUVEC after preincubation with the same mAb.

Citation of a reference herein shall not be construed as an admission that such reference is prior art to the present invention.

3. SUMMARY OF THE INVENTION

The present invention is directed to a method for isolating a novel receptor for α4 integrins, that are distinct from VCAM-1 and from fibronectin. The term "α4 integrins" as used herein shall mean molecules comprising the α4 integrin subunit, including but not limited to VLA-4 (α4β1), α4β7, and the α4 subunit itself. Isolated nucleic acids encoding the receptor and antibodies to the receptor are also provided. The invention is also directed to pharmaceutical compositions, and methods of treating disorders involving an undesirable inflammatory or immune response by administering the VLA-4 receptor of the invention.

3.1. DEFINITIONS

As used herein, the following terms shall have the indicated meanings.

HUVEC, human umbilical vein endothelial cells.
ICAM, intercellular adhesion molecule.
Ig, immunoglobulin.
LFA-1, lymphocyte function-associated antigen-1.
mAb, monoclonal antibody.
PBL, peripheral blood lymphocytes.
TNF, tumor necrosis factor.
VCAM-1, vascular cell adhesion molecule-1.
VCAM-6D, six Ig domain form of VCAM-1.
VCAM-7D, seven Ig domain form of VCAM-1.
VLA-4, very late activation antigen-4.

4. DESCRIPTION OF THE FIGURES

FIG. 1: JY cell binding to 2 hr TNF-stimulated HUVEC. Before binding, JY cells were incubated with control medium or with mAb TS1/22 (anti-LFA-1). Results are from one experiment with error bars indicating one standard deviation (SD) of four replicates.

Figure 2A:
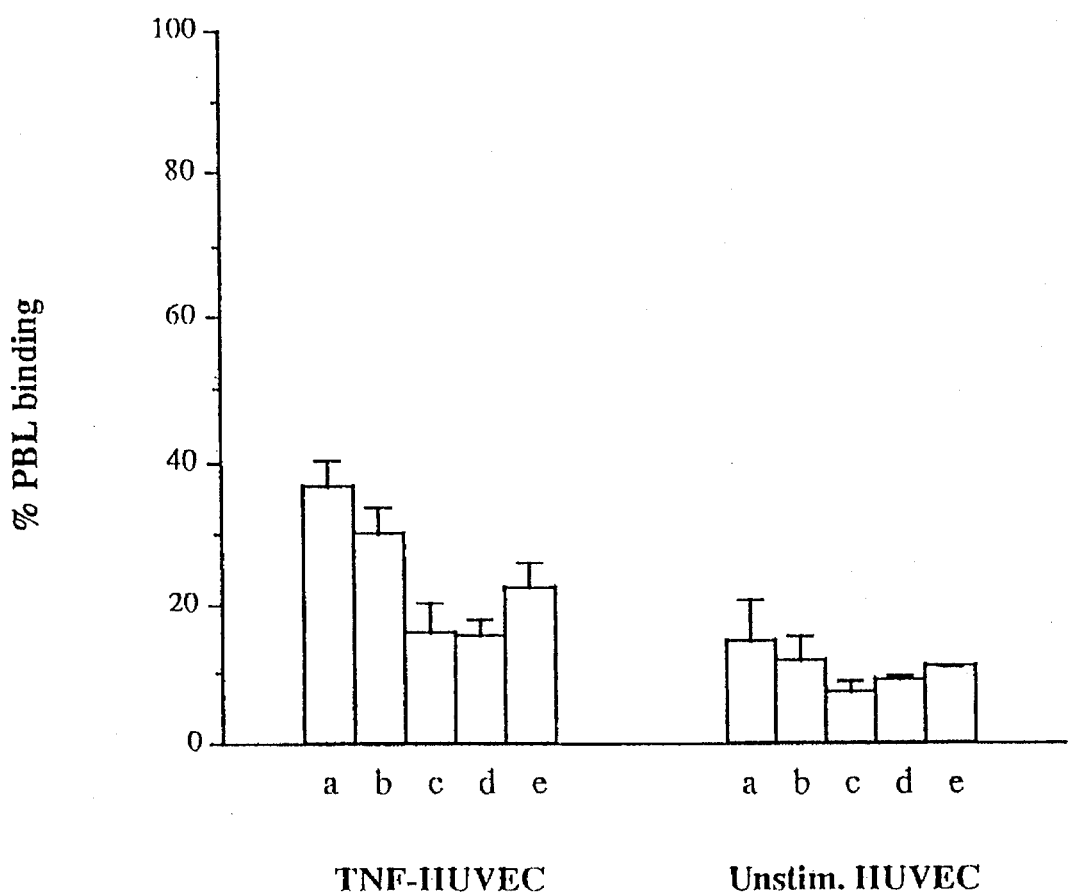
Figure 2B:
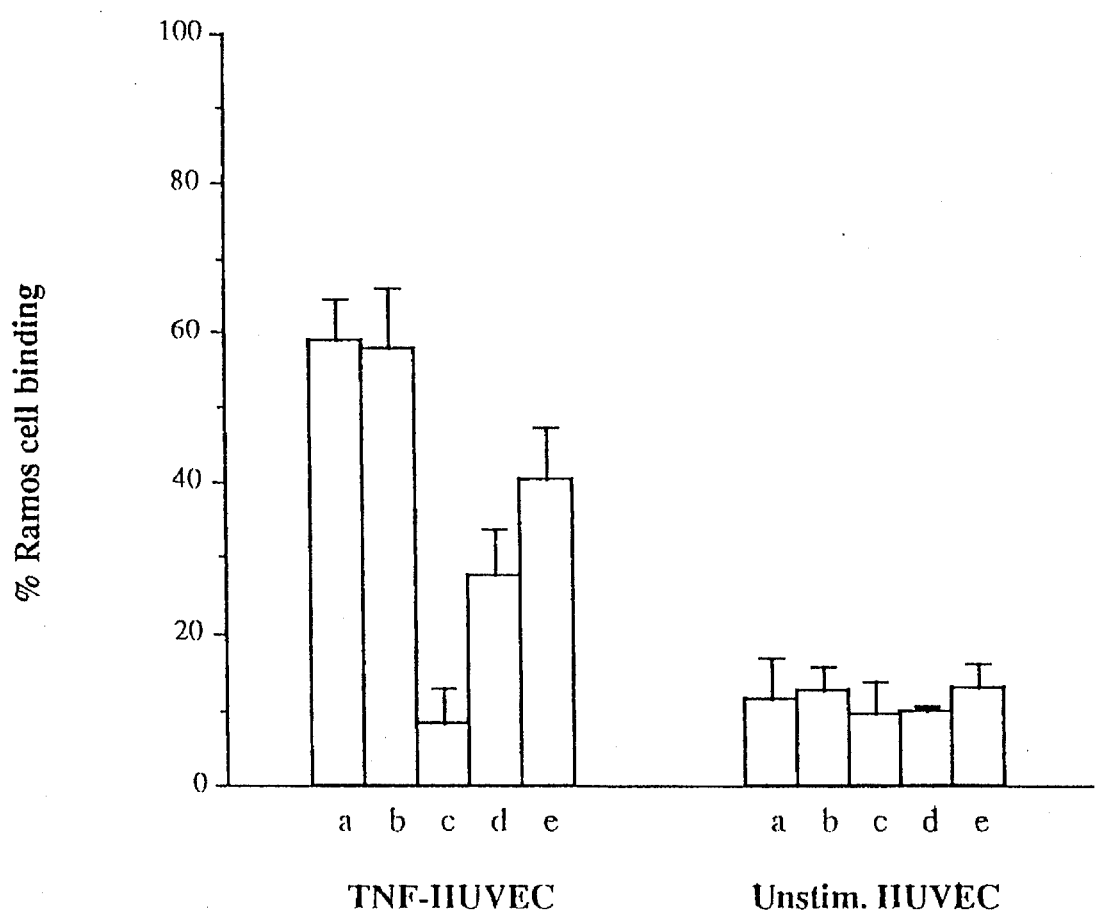
Figure 2C:
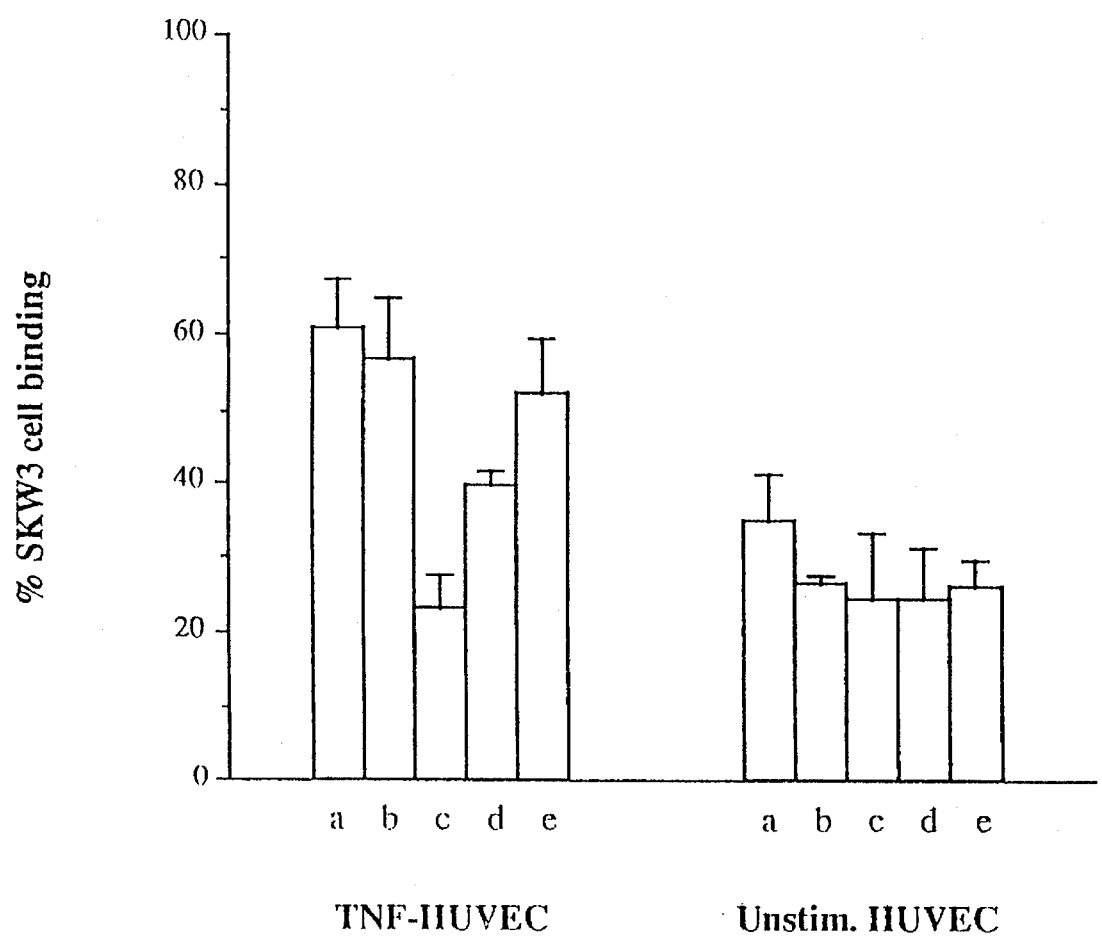

FIG. 2A–2C: Binding of (A) PBL or (B) Ramos or (C) SKW3 lymphoid tumor cells to HUVEC stimulated for 24 hr with TNF or to unstimulated HUVEC. Error bars represent one SD of the mean of three to eight experiments performed in quadruplicate. a, control medium; b, TS1/22 (anti-LFA-1); c, TS1/22 (anti-LFA-1) +HP2/1 (anti-VLA-4); d, TS1/22 (anti-LFA-1)+4B9 (anti-VCAM-1); e, TS1/22 (anti-LFA-1)+E1/6 (anti-VCAM-1).

Figure 3A:
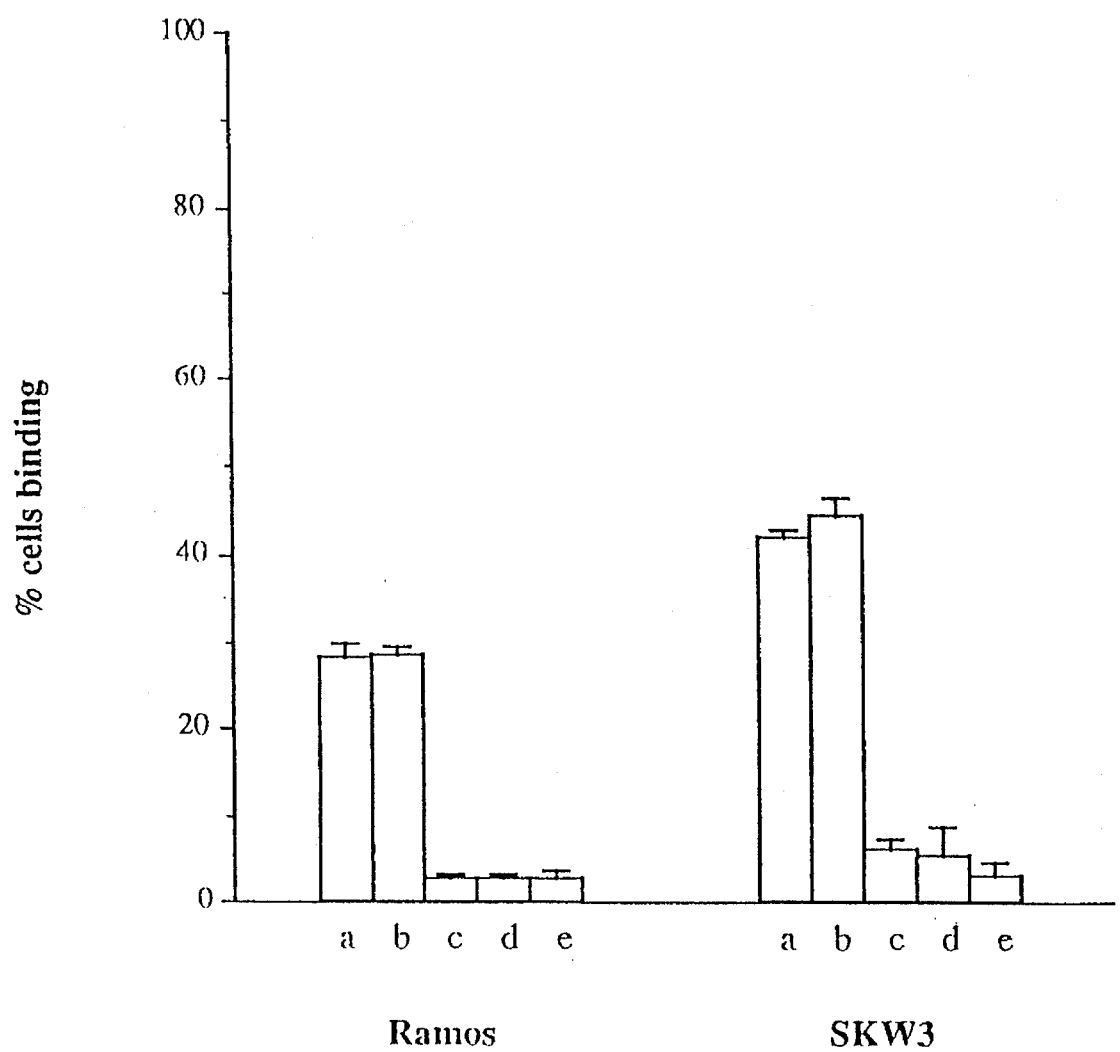

FIG. 3A: Ramos and SKW3 cell binding to fibronectin coated on plastic. Error bars represent one SD of the mean of three experiments performed in quadruplicate. a, control medium; b, TS1/22 (anti-LFA-1); c, HP2/1 (anti-VLA-4); d, goat anti-fibronectin; e, To BSA.

Figure 3B:
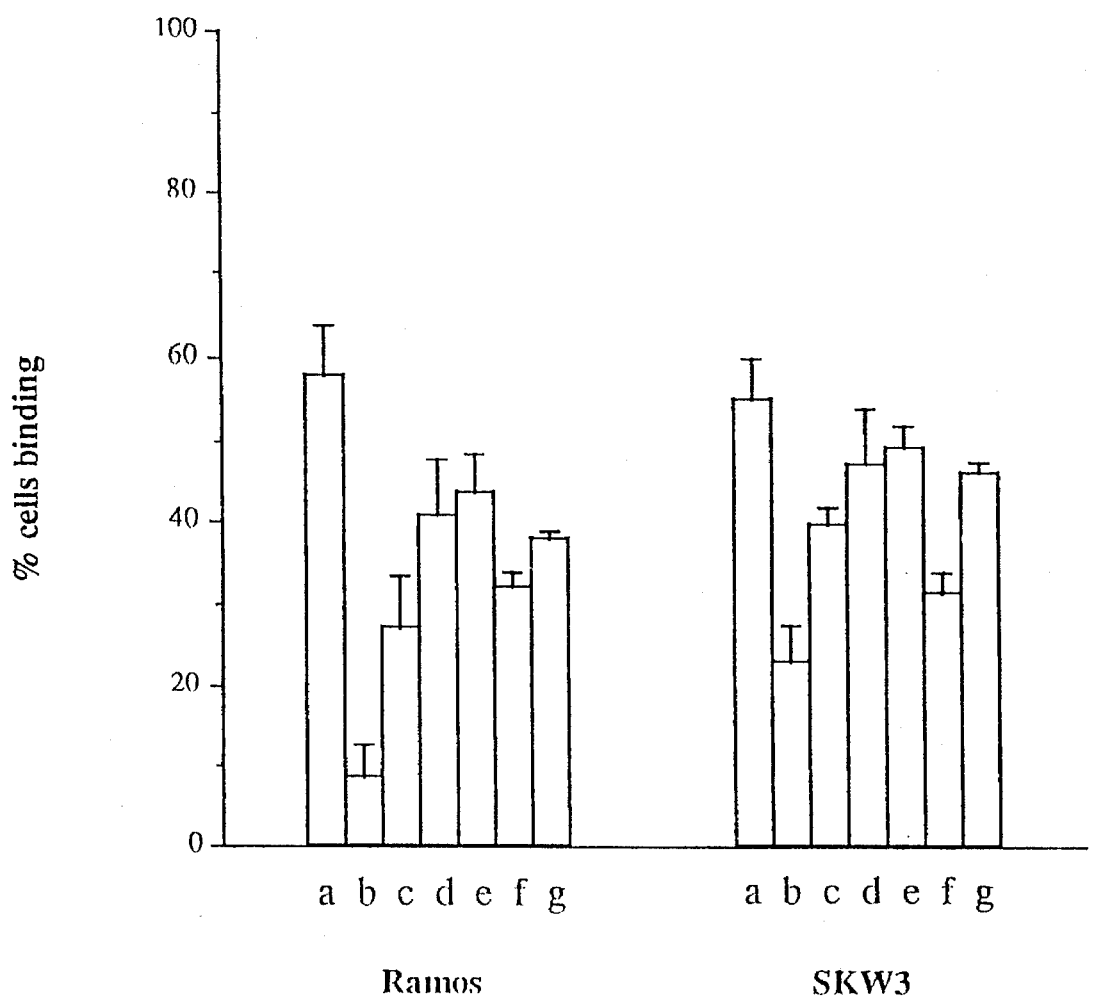

FIG. 3B: Ramos and SKW3 cell binding to 24 hr TNF-stimulated HUVEC. Error bars represent one SD of the mean of three experiments performed in quadruplicate. a, control medium; b, TS1/22 (anti-LFA-1)+HP2/1 (anti-VLA-4); c, TS1/22 (anti-LFA-1)+4B9 (anti-VCAM-1); d, TS1/22 (anti-LFA-1)+E1/6 (anti-VCAM-1); e, TS1/22 (anti-LFA-1)+goat anti-fibronectin; f, TS1/22 (anti-LFA-1)+4B9 (anti-VCAM-1)+goat anti-fibronectin; g, TS1/22 (anti-LFA-1)+E1/6 (anti-VCAM-1)+goat anti-fibronectin.

FIG. 4: Comparison of VLA-4-dependent vs. VLA-dependent/E1/6-dependent adhesion of Ramos cells to HUVEC as functions of time of TNF stimulation. Error bars represent one SD of the mean of five experimental calculations. The means of the raw data on which these calculations were based are also shown ±1 SD. Closed circles, VLA-4-dependent; open squares, VLA-4-dependent/E1/6-dependent.

5. DETAILED DESCRIPTION OF THE INVENTION

The present invention is directed to a method for the identification and isolation of a receptor (hereinafter, the "Receptor") for α4 integrins, which Receptor is distinct from VCAM-1 and fibronectin. The term "α4 integrins" as used herein shall mean molecules comprising the α4 integrin subunit, including but not limited to VLA-4 (an α4β1 heterodimer), α4β7 (Chan et al., 1992, J. Biol. Chem. 267:8366–8370), and the α4 subunit itself. As described in the examples sections infra, we assessed adhesion of PBL and lymphoid cell lines to stimulated and unstimulated HUVEC and compared the inhibitory effects of anti-VLA-4 and anti-VCAM-1 mAb. Anti-fibronectin antiserum was also studied to assess the role of fibronectin in lymphocyte-endothelial cell interactions. Our findings regarding cell line adhesion to HUVEC provide evidence for an inducible α4 integrin counter-receptor distinct from VCAM-1 or fibronectin.

This novel Receptor for α4 integrin, in preferred aspects, is isolated by (i) functional cloning, or (ii) generation of an antibody to such Receptor and isolation of the Receptor by procedures based on binding to its antibody. Specific embodiments of such methods are detailed in the sections infra.

5.1. ISOLATION OF THE α4 INTEGRIN RECEPTOR GENE

The invention relates to the nucleotide sequences encoding the Receptor consisting of at least 8 nucleotides (i.e., a hybridizable portion). In a specific embodiment, the invention relates to such nucleic acid sequences consisting of at least 50 nucleotides, or at least 200 nucleotides. The invention also relates to nucleic acids hybridizable to or complementary to the foregoing sequences. Hybridization can be carried out under any conditions known in the art. For example, a highly homologous nucleic acid will hybridize to the Receptor DNA under conditions of high stringency (e.g., 0.1 X SSC at a temperature of about 65° C.). The stringency can be lowered to allow hybridization of less homologous nucleic acids.

Nucleic acids encoding fragments and derivatives of the Receptor (see infra) are additionally provided.

A preferred embodiment for the functional cloning of a cDNA encoding a Receptor, presented as particular examples but not by way of limitation, follows (see also Section 7):

In a first specific embodiment, briefly, functional cloning of the Receptor can be carried out by transfecting cells with a cDNA library (preferably synthesized from stimulated endothelial cell mRNA), incubating the cells in VLA-4 coated plastic dishes with an anti-VCAM-1 mAb that blocks binding of VLA-4 to VCAM-1 and preferably also with an anti-fibronectin antiserum that blocks binding of VLA-4 to fibronectin, and recovering plasmid from adherent cells. The cDNA can be expressed to produce recombinant Receptor as described infra.

Other specific embodiments for functional cloning of a Receptor are described in Section 7 infra.

The above-mentioned methods are not meant to limit the following general description of methods by which clones of the Receptor may be obtained.

Any eukaryotic cell potentially can serve as the nucleic acid source for the molecular cloning of the Receptor gene. Endothelial cell cDNA is preferred. The nucleic acid sequences encoding Receptor can be isolated from human, porcine, bovine, feline, avian, equine, canine, as well as additional primate sources, etc. The DNA may be obtained by standard procedures known in the art from cloned DNA (e.g., a DNA "library"), by chemical synthesis, by cDNA cloning, or by the cloning of genomic DNA, or fragments thereof, purified from the desired cell. (See, for example, Sambrook et al., 1989, Molecular Cloning, A Laboratory Manual, 2d Ed., Cold Spring Harbor Laboratory Press, Cold Spring Harbor, New York; Glover, D. M. (ed.), 1985, DNA Cloning: A Practical Approach, MRL Press, Ltd., Oxford, U.K. Vol. I, II.) Clones derived from genomic DNA may contain regulatory and intron DNA regions in addition to coding regions; clones derived from cDNA will contain only exon sequences. Whatever the source, the gene should be molecularly cloned into a suitable vector for propagation of the gene.

In a specific embodiment, PCR is used to amplify the desired sequence in a library, prior to selection. Oligonucleotide primers representing known Receptor sequences can be used as primers in PCR. The synthetic oligonucleotides may be utilized as primers to amplify by PCR sequences from a source (RNA or DNA), preferably a cDNA library, of potential interest. PCR can be carried out, e.g., by use of a Perkin-Elmer Cetus thermal cycler and Taq polymerase (Gene Amp™). The DNA being amplified can include mRNA or cDNA or genomic DNA from any eukaryotic species. One can choose to synthesize several different degenerate primers, for use in the PCR reactions. It is also possible to vary the stringency of hybridization conditions used in priming the PCR reactions, to allow for greater or lesser degrees of nucleotide sequence similarity between the Receptor homolog and the known Receptor. After successful amplification of a segment of a Receptor homolog, that segment may be molecularly cloned and sequenced, and utilized as a probe to isolate a complete cDNA or genomic clone. This, in turn, will permit the determination of the gene's complete nucleotide sequence, the analysis of its expression, and the production of its protein product for functional analysis, as described infra. In this fashion, additional genes encoding the Receptor may be identified.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene may be accomplished in a number of ways. For example, if an amount of a portion of the Receptor gene or its specific RNA, or a fragment thereof, e.g., an extracellular domain, is available and can be purified and labeled, the generated DNA fragments may be screened by nucleic acid hybridization to the labeled probe (Benton, W. and Davis, R., 1977, Science 196:180; Grunstein, M. And Hogness, D., 1975, Proc. Natl. Acad. Sci. U.S.A. 72:3961). Those DNA fragments with substantial homology to the probe will hybridize. It is also possible to identify the appropriate fragment by restriction enzyme digestion(s) and comparison of fragment sizes with those expected according to a known restriction map if such is available. Further selection can be carried out on the basis of the properties of the gene. Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, VLA-4 or other α4 integrin binding activity, or antigenic properties as known for the Receptor. If an antibody to the Receptor is available, the Receptor protein may be identified by binding of labeled antibody to the putatively Receptor synthesizing clones, in an ELISA (enzyme-linked immunosorbent assay)-type procedure.

The Receptor gene can also be identified by mRNA selection by nucleic acid hybridization followed by in vitro translation. In this procedure, fragments are used to isolate complementary mRNAs by hybridization. Such DNA fragments may represent available, purified Receptor DNA of another species. Immunoprecipitation analysis or functional assays (e.g., VLA-4 binding ability in vitro) of the in vitro translation products of the isolated products of the isolated mRNAs identifies the mRNA and, therefore, the complementary DNA fragments that contain the desired sequences. In addition, specific mRNAs may be selected by adsorption of polysomes isolated from cells to immobilized antibodies specifically directed against Receptor protein. A radiolabelled Receptor cDNA can be synthesized using the selected mRNA (from the adsorbed polysomes) as a template. The radiolabelled mRNA or cDNA may then be used as a probe to identify the Receptor DNA fragments from among other genomic DNA fragments.

Alternatives to isolating the Receptor genomic DNA include, but are not limited to, chemically synthesizing the gene sequence itself from a known sequence or making cDNA to the mRNA which encodes the Receptor protein. For example, RNA for cDNA cloning of the Receptor gene can be isolated from cells which express the Receptor. Other methods are possible and within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as PBR322 or pUC plasmid derivatives. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and Receptor gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionation, can be done before insertion into the cloning vector.

In specific embodiments, transformation of host cells with recombinant DNA molecules that incorporate the isolated Receptor gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

5.2. RECOMBINANT EXPRESSION OF THE α4 INTEGRIN RECEPTOR

The nucleotide sequence coding for the Receptor of the invention or a functionally active fragment or other derivative thereof can be inserted into an appropriate expression vector, i.e., a vector which contains the necessary elements for the transcription and translation of the inserted protein-coding sequence. The necessary transcriptional and translational signals can also be supplied by the native gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. In a specific embodiment, a sequence encoding a functionally active portion of the Receptor is expressed. In yet another embodiment, a fragment of the Receptor comprising the extracellular domain, or intracellular domain, or transmembrane region, or any combination of the foregoing, is expressed.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of nucleic acid sequence encoding the VLA-4 Receptor or fragment thereof may be regulated by a second nucleic acid sequence so that the Receptor protein or peptide is expressed in a host transformed with the recombinant DNA molecule. For example, expression of the Receptor may be controlled by any promoter/enhancer element known in the art. Promoters which may be used to control Receptor gene expression include, but are not limited to, the SV40 early promoter region (Bernoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; plant expression vectors comprising the nopaline synthetase promoter region (Herrera-Estrella et al., Nature 303:209–213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58; alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94; myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Expression vectors containing the α4 Receptor gene inserts can be identified by three general approaches: (a) nucleic acid hybridization, (b) presence or absence of "marker" gene functions, and (c) expression of inserted sequences. In the first approach, the presence of a foreign gene inserted in an expression vector can be detected by nucleic acid hybridization using probes comprising sequences that are homologous to the inserted Receptor gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the Receptor gene is inserted within the marker gene sequence of the vector, recombinants containing the Receptor insert can be identified by the absence of the marker gene function. In the third approach, recombinant expression vectors can be identified by assaying the foreign gene product expressed by the recombinant. Such assays can be based, for example, on the physical or functional properties of the Receptor gene product in in vitro assay systems, e.g., binding to VLA-4, binding to α4β7, binding with antibody.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered Receptor protein may be controlled. Furthermore, different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a heterologous Receptor protein. Furthermore, different vector/host expression systems may effect processing reactions such as proteolytic cleavages to different extents.

Vectors are introduced into the desired host cells by methods known in the art, e.g., transfection, electroporation, microinjection, transduction, etc.

Both cDNA and genomic sequences can be cloned and expressed.

5.3. PURIFICATION OF THE α4 INTEGRIN RECEPTOR

Once a recombinant which expresses the Receptor gene sequence is identified, the gene product can be analyzed. This is achieved by assays based on the physical or functional properties of the product, including radioactive labelling of the product followed by analysis by gel electrophoresis, immunoassay, etc.

Once the Receptor protein is identified, it may be isolated and purified by standard methods including chromatography (e.g., ion exchange, affinity, and sizing column chromatography), centrifugation, differential solubility, or by any other standard technique for the purification of proteins. The functional properties may be evaluated using any suitable assay (see Section 5.6).

Alternatively, once a Receptor protein produced by a recombinant is identified, the amino acid sequence of the protein can be deduced from the nucleotide sequence of the chimeric gene contained in the recombinant. As a result, the protein can be synthesized by standard chemical methods known in the art (e.g., see Hunkapiller, M., et al., 1984, Nature 310:105–111).

In a preferred aspect, by way of example but not limitation, isolation via antibody binding can be carried out by using endothelial cells as immunogen to generate hybridomas, and screening hybridomas according to the assays described in Section 5.7.1 to select neutralizing antibodies. Alternatively, cells (e.g., COS cells) transfected with a Receptor cDNA clone are used as immunogen, and the hybridomas are assayed as described in Section 5.7.1 to select neutralizing antibodies. Alternatively, since it is not necessary that the antibody be neutralizing, hybridomas can be screened by any method known in the art for binding to the Receptor, e.g., by detecting staining of COS cells transfected with a Receptor cDNA clone. The antibody which is then selected by screening according to any of such methods is then recovered and used to isolate the Receptor protein by immunospecific binding thereto. For example, the Receptor is immunoprecipitated from protein lysates of stimulated human umbilical vein endothelial cells by incubation of the lysates with antibody-bound Sepharose beads, whereby a complex is formed between the antibody and the Receptor in the lysate. The beads are then washed to remove unbound protein in the lysates, and the Receptor protein is recovered from the antibody-Receptor complex. (See also Section 8.)

Further purification can be carried out by methods known in the art (see also Section 5.3).

5.4. STRUCTURE OF THE RECEPTOR GENE AND PROTEIN

The structure of the Receptor gene and protein can be analyzed by various methods known in the art.

5.4.1. GENETIC ANALYSIS

The cloned DNA or cDNA corresponding to the Receptor gene can be analyzed by methods including but not limited to Southern hybridization (Southern, E. M., 1975, J. Mol. Biol. 98:503–517), Northern hybridization (see e.g., Freeman et al., 1983, Proc. Natl. Acad. Sci. U.S.A. 80:4094–4098), restriction endonuclease mapping (Maniatis, T., 1982, Molecular Cloning, A Laboratory, Cold Spring Harbor, New York), and DNA sequence analysis. Polymerase chain reaction (PCR; U.S. Pat. Nos. 4,683,202, 4,683,195 and 4,889,818; Gyllenstein et al., 1988, Proc. Natl. Acad. Sci. U.S.A. 85:7652–7656; Ochman et al., 1988, Genetics 120:621–623; Loh et al., 1989, Science 243:217–220) followed by Southern hybridization with a Receptor-specific probe can allow the detection of the Receptor gene in DNA from various cell types. The stringency of the hybridization conditions for both Southern and Northern hybridization can be manipulated to ensure detection of nucleic acids with the desired degree of relatedness to the specific Receptor probe used.

Restriction endonuclease mapping can be used to roughly determine the genetic structure of the Receptor gene. Restriction maps derived by restriction endonuclease cleavage can be confirmed by DNA sequence analysis.

DNA sequence analysis can be performed by any techniques known in the art, including but not limited to the method of Maxam and Gilbert (1980, Meth. Enzymol. 65:499–560), the Sanger dideoxy method (Sanger, F., et al., 1977, Proc. Natl. Acad. Sci. U.S.A. 74:5463), the use of T7 DNA polymerase (Tabor and Richardson, U.S. Pat. No. 4,795,699), or use of an automated DNA sequenator (e.g., Applied Biosystems, Foster City, Calif.).

5.4.2. PROTEIN ANALYSIS

The amino acid sequence of the Receptor protein can be derived by deduction from the DNA sequence, or alternatively, by direct sequencing of the protein, e.g., with an automated amino acid sequencer.

The Receptor protein sequence can be further characterized by a hydrophilicity analysis (Hopp, T. and Woods, K., 1981, Proc. Natl. Acad. Sci. U.S.A. 78:3824). A hydrophilicity profile can be used to identify the hydrophobic and hydrophilic regions of the Receptor protein and the corresponding regions of the gene sequence which encode such regions.

Secondary, structural analysis (Chou, P. and Fasman, G., 1974, Biochemistry 13:222) can also be done, to identify regions of the Receptor protein that assume specific secondary structures.

Manipulation, translation, and secondary structure prediction, as well as open reading frame prediction and plotting, can also be accomplished using computer software programs available in the art.

Other methods of structural analysis can also be employed. These include but are not limited to X-ray crystallography (Engstom, A., 1974, Biochem. Exp. Biol. 11:7–13) and computer modeling (Fletterick, R. and Zoller, M. (eds.), 1986, Computer Graphics and Molecular Modeling, in Current Communications in Molecular Biology, Cold Spring Harbor Laboratory, Cold Spring Harbor, N.Y.).

5.5. DERIVATIVES AND ANALOGS OF THE RECEPTOR

The invention further relates to derivatives (including but not limited to fragments) and analogs of the Receptor proteins of the invention.

The production and use of derivatives and analogs related to the Receptor are within the scope of the present invention. In a specific embodiment, the derivative or analog is functionally active, i.e., capable of exhibiting one or more functional activities associated with the full-length, wild-type Receptor protein. As one example, such derivatives or analogs which have the desired immunogenicity or antigenicity can be used, for example, in immunoassays, for immunization, for inhibition of Receptor activity, etc. Such molecules which retain, or alternatively inhibit, a desired Receptor property, e.g., binding to VLA-4 or other ligand having an $\alpha 4$ integrin subunit, can be used as inducers, or inhibitors, respectively, of such property and its physiological correlates. Derivatives or analogs of the Receptor can be tested for the desired activity by procedures known in the art, including but not limited to assays described in Section 6.

In particular, Receptor derivatives can be made by altering Receptor sequences by substitutions, additions or deletions that provide for functionally equivalent molecules. Due to the degeneracy of nucleotide coding sequences, other DNA sequences which encode substantially the same amino acid sequence as a Receptor gene may be used in the practice of the present invention. These include but are not limited to nucleotide sequences comprising all or portions of Receptor genes which are altered by the substitution of different codons that encode a functionally equivalent amino acid residue within the sequence, thus producing a silent change. Likewise, the Receptor derivatives of the invention include, but are not limited to, those containing, as a primary amino acid sequence, all or part of the amino acid sequence of a Receptor protein including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Derivatives or analogs of a Receptor include but are not limited to those peptides which are substantially homologous to a Receptor or fragments thereof, or whose encoding nucleic acid is capable of hybridizing to a Receptor nucleic acid sequence.

The Receptor derivatives and analogs of the invention can be produced by various methods known in the art. The manipulations which result in their production can occur at the gene or protein level. For example, the cloned Receptor gene sequence can be modified by any of numerous strategies known in the art (Maniatis, T., 1990, Molecular Cloning, A Laboratory Manual, 2d ed., Cold Spring Harbor Laboratory, Cold Spring Harbor, New York). The sequence can be cleaved at appropriate sites with restriction endonuclease(s), followed by further enzymatic modification if desired, isolated, and ligated in vitro. In the production of the gene encoding a derivative or analog of Receptor, care should be taken to ensure that the modified gene remains within the same translational reading frame as the Receptor, uninterrupted by translational stop signals, in the gene region where the desired Receptor activity is encoded.

Additionally, the Receptor-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem 253:6551), use of TAB® linkers (Pharmacia), etc.

Manipulations of the Receptor sequence may also be made at the protein level. Included within the scope of the invention are Receptor protein fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

In addition, analogs and derivatives of a Receptor can be chemically synthesized. For example, a peptide corresponding to a portion of a Receptor protein which comprises the desired domain (e.g., extracellular, intracellular, transmembrane, or any combination thereof), or which mediates the desired activity in vitro, e.g., binding to an $\alpha 4$ integrin subunit, can be synthesized by use of a peptide synthesizer. Furthermore, if desired, nonclassical amino acids or chemical amino acid analogs can be introduced as a substitution or addition into the Receptor sequence. Non-classical amino acids include but are not limited to the D-isomers of the common amino acids, $\alpha$-amino isobutyric acid, 4-aminobutyric acid, hydroxyproline, sarcosine, citrulline, cysteic acid, t-butylglycine, t-butylalanine, phenylglycine, cyclohexylalanine, $\beta$-alanine, designer amino acids such as $\beta$-methyl amino acids, $C\alpha$-methyl amino acids, and $N\alpha$-methyl amino acids.

In a specific embodiment, the Receptor derivative is a chimeric, or fusion, protein comprising a Receptor protein or fragment thereof fused to a non-Receptor amino acid sequence. In one embodiment, such a chimeric protein is produced by recombinant expression of a nucleic acid encoding the protein (comprising a Receptor-coding sequence joined in-frame to a non-Receptor coding sequence). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

5.6. ASSAYS OF RECEPTOR PROTEINS, DERIVATIVES AND ANALOGS

The functional activity of Receptor proteins, derivatives and analogs can be assayed by various methods.

For example, in one embodiment, where one is assaying for the ability to bind or compete with wild-type Receptor for binding to anti-Receptor antibody, various immunoassays known in the art can be used, including but not limited to competitive and noncompetitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present invention.

In another embodiment, where one is assaying for the ability to mediate binding to VLA-4 or the α4 integrin subunit, one can carry out an in vitro binding assay such as described infra in Section 6, e.g., to see if addition of soluble or solubilized Receptor will decrease binding of lymphoid cell line to HUVEC, or assay directly for the ability to bind to VLA-4 coated on plastic dishes.

5.7. GENERATION AND USE OF ANTIBODIES TO THE α4 INTEGRIN RECEPTOR

According to the invention, the α4 Receptor protein, its fragments or other derivatives, or analogs thereof, or cells expressing the foregoing may be used as an immunogen to generate antibodies which recognize such an immunogen. Such antibodies include but are not limited to polyclonal, monoclonal, chimeric, single chain, Fab fragments, and an Fab expression library. In a specific embodiment, antibodies to the human VLA-4 Receptor are produced. In another embodiment, antibodies to the extracellular domain of the Receptor are produced. In another embodiment, antibodies to the intracellular domain of the Receptor are produced. In a preferred aspect, a monoclonal antibody to the Receptor is obtained by the method described in Section 8, infra. In a specific embodiment, COS cells transfected with a cDNA clone encoding the Receptor are used as immunogen.

Various procedures known in the art may be used for the production of polyclonal antibodies to the Receptor protein or derivative or analog. In a particular embodiment, rabbit polyclonal antibodies to an epitope of the Receptor protein can be obtained. For the production of antibody, various host animals can be immunized by injection with the native Receptor protein, or a synthetic version, or derivative (e.g., fragment) thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

For preparation of monoclonal antibodies directed toward the Receptor protein or analog thereof, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:721), and the EBV-hybridoma technique to produce human monoclonal antibodies (Cole et al., 1985, in Monoclonal Antibodies and Cancer Therapy, Alan R. Liss., Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in Monoclonal Antibodies and Cancer Therapy, Alan R. Liss, pp. 77–96). In fact, according to the invention, techniques developed for the production of "chimeric antibodies" (Morrison et al., 1984, Proc. Natl. Acad. Sci. U.S.A. 81:6851–6855; Neuberger et al., 1984, Nature 312:604–608; Takeda et al., 1985, Nature 314:452–454) by splicing the genes or portions thereof (e.g., hypervariable regions) from a mouse antibody molecule specific for the Receptor together with genes from a human antibody molecule (e.g., the constant regions) of appropriate biological activity can be used; such antibodies are within the scope of this invention.

According to the invention, techniques described for the production of single chain antibodies (U.S. Pat. No. 4,946,778) can be adapted to produce Receptor-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for the Receptor proteins, derivatives, or analogs.

Antibody fragments which contain the idiotype (binding domain) of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g. ELISA (enzyme-linked immunosorbent assay). For example, to select antibodies which recognize a specific domain of the Receptor protein, one may assay generated hybridomas for a product which binds to a Receptor fragment containing such domain.

The foregoing antibodies can be used in methods known in the art relating to the localization and activity of the protein sequences of the invention (e.g., see Section 5.7, infra), e.g., for imaging these proteins, measuring levels thereof in appropriate physiological samples, etc.

5.7.1. ASSAYS FOR NEUTRALIZING ANTIBODIES

Antibodies to the Receptor which are neutralizing (i.e., block binding of the Receptor (either purified or expressed on a cell surface) to an α4 integrin (either purified or expressed on a cell surface) can be identified by assays such as those described below.

In one embodiment, hybridomas are screened for the ability of their secreted antibodies to inhibit stimulated endothelial cell binding to (α4 integrin-expressing) lymphoid cell lines in the presence of an anti-VCAM-1 mAb that blocks binding of the α4 integrin to VCAM-1, and preferably also in the presence of an anti-fibronectin antiserum that blocks binding of the α4 integrin to fibronectin. If the lymphoid cell lines express LFA-1 (e.g., Ramos, SKW3), the screening should also be in the presence of anti-LFA-1 antibody. An antibody with such ability is selected.

In another embodiment, hybridomas are screened for the ability of their secreted antibodies to inhibit binding of stimulated endothelial cells to purified VLA-4 (and/or other purified α4 integrin(s)) coated on a solid phase surface such as plastic, in the presence of an anti-VCAM-1 mAb that blocks binding of VLA-4 (or the other α4 integrin) to VCAM.-1, and preferably also in the presence of an anti-fibronectin antiserum that blocks binding of VLA-4 (or the other α4 integrin) to fibronectin. An antibody with such ability is selected.

In yet another embodiment, in which a cDNA clone encoding the receptor is available, hybridomas are screened for the ability of their secreted antibodies to inhibit binding of cells (e.g., transfected COS cells) expressing a Receptor cDNA to (α4 integrin-expressing) cells of a lymphoid cell line. An antibody with such ability is selected.

In yet another embodiment, in which a cDNA clone encoding the receptor is available, hybridomas are screened for the ability of their secreted antibodies to inhibit binding of cells (e.g., transfected COS cells) expressing a Receptor cDNA to purified VLA-4 (or other α4 integrin) coated on a solid phase surface such as plastic. An antibody with such ability is selected.

5.8. IDENTIFICATION OF INHIBITORS OF THE BINDING OF AN α4 INTEGRIN TO THE α4 INTEGRIN RECEPTOR

The present invention also provides screening methods, for identifying molecules with the ability to inhibit binding of an α4 integrin to the Receptor of the invention. Molecules with such an inhibitory ability are termed herein "α4 inhibitors." Such α4 inhibitors are identified by detecting their ability to inhibit binding of an α4 integrin to the Receptor, e.g., as set forth in the following exemplary methods:

In one embodiment, a molecule is screened for the ability to inhibit cells of a lymphoid cell line from binding to stimulated endothelial cells in the presence of an anti-VCAM-1 mAb that blocks binding of VLA-4 to VCAM-1, and preferably also in the presence of an antiserum to fibronectin that blocks binding of VLA-4 to fibronectin. If the lymphoid cells (e.g., Ramos, SKW3) express LFA-1, the screening is preferably also carried out in the presence of an anti-LFA-1 mAb that blocks binding of LFA-1 to its counter-receptors ICAM-1 and ICAM-2.

In another embodiment, a molecule is screened for the ability to inhibit cells of a lymphoid cell line from binding to cells (e.g., transfected COS cells) expressing a Receptor cDNA.

In another embodiment, a molecule is screened for the ability to inhibit stimulated endothelial cells from binding to purified VLA-4 (and/or other purified α4 integrin(s)) on a solid surface such as plastic, in the presence of an anti-VCAM-1 mAb that blocks binding of VLA-4 (or the other α4 integrin) to VCAM-1, and preferably also in the presence of an antiserum to fibronectin that blocks binding of VLA-4 (or the other α4 integrin) to fibronectin.

In another embodiment, a molecule is screened for the ability to inhibit cells (e.g., transfected COS cells) expressing a Receptor cDNA from binding to purified VLA-4 (and/or other purified α4 integrin(s)) on a solid surface such as plastic.

5.9. THERAPEUTIC USES OF THE α4 INTEGRIN RECEPTOR, ANTIBODIES THERETO, AND α4 INHIBITORS

The Receptor and analogs and derivatives (including fragments) thereof, and neutralizing antibodies thereto and antibody derivatives, and α4 inhibitors of the invention (collectively termed herein "Therapeutics") have use therapeutically in diseases or disorders involving inflammation, and which involve extravasation of leukocytes (inflammatory and immune disorders). The invention provides methods of reducing inflammation, and of treating or preventing disorders associated therewith, by administration to a subject of an effective amount of a Therapeutic of the invention. The subject is preferably an animal, including but not limited to animals such as cows, pigs, chickens, etc., and is preferably a mammal, and most preferably human.

Diseases and disorders which can be treated by administration of a therapeutically effective amount of a Therapeutic include but are not limited to the following:

Inflammatory arthritis—e.g., rheumatoid arthritis, seronegative spondeloarthritites (Behcets disease, Reiter's syndrome, etc.), juvenile rheumatoid arthritis, vasculitis, psoriatic arthritis, polydermatomyositis.

Systemic lupus erythematosus (SLE).

Asthma.

Inflammatory dermatoses—e.g., psoriasis, dermatitis herpetiformis, eczema, necrotizing and cutaneous vasculitis, bullous diseases.

Reperfusion injury.

Septic shock (Sepsis).

Adult respiratory distress syndrome (ARDS).

Tissue damage relating to tissue transplantation.

Other autoimmune disorders. In addition to the autoimmune disorders SLE and rheumatoid arthritis, disorders such as glomerulonephritis, juvenile onset diabetes, multiple sclerosis, allergic conditions, autoimmune thyroiditis, allograft rejection (e.g., rejection of transplanted kidney, heart, or liver), Crohn's disease, and graft-versus-host disease can be treated.

Thermal injury (burn). The main complications due to burn are inflammatory in nature, including shock, and pulmonary edema.

Cardiopulmonary bypass. Systemic inflammation has been associated with the use of pump-oxygenator systems in cardiopulmonary bypass and hemodialysis, which can lead to organ dysfunction, termed the post-pump syndrome or post-perfusion syndrome.

In addition, other diseases and clinical correlates of undesirable inflammatory responses can be treated with Therapeutics of the invention, including but not limited to those associated with hemolytic anemia, hemodialysis, blood transfusion, certain hematologic malignancies, pneumonia, postischemic myocardial inflammation and necrosis, barotrauma (decompression sickness), ulcerative colitis, inflammatory bowel disease, atherosclerosis, cytokine-induced toxicity, necrotizing enterocolitis, granulocyte-transfusion-associated syndromes, Reynaud's syndrome, multiple organ injury syndromes secondary to septicemia or trauma, and acute purulent meningitis or other central nervous system inflammatory disorders.

5.9.1. DEMONSTRATION OF THERAPEUTIC UTILITY

The Therapeutics of the invention can be tested in vivo for the desired anti-inflammatory activity. For example, such compounds can be tested in suitable animal model systems prior to testing in humans, including but not limited to rats, mice, chicken, cows, monkeys, rabbits, etc. Suitable model systems are also used to demonstrate therapeutic utility (see infra).

For in vivo testing, prior to administration to humans, any animal model system known in the art may be used. For example, several animal models are available to demonstrate the efficacy of a Therapeutic of the invention in the treatment of adult respiratory distress syndrome (ARDS). These include New Zealand white rabbits infused with activated complement (Nuytinck et al., 1986, Brit. J. Exp. Pathol. 67:537–548); cerulean-induced acute pancreatitis in rats (Guice et al., 1988, Ann. Surg. 208:71–77); a porcine model produced by infusion of live *Pseudomonas aeruginosa* (Dehring et al., 1987, J. Trauma 27:615–625); cynomolgus monkeys (*Macaca fascicularis*) made acutely septic with infusions of *E. coli*, resulting in severe sepsis and ARDS (Stevens et al., 1986, J. Clin. Invest. 77:1812–1816).

Two animal models of sepsis which can be used are a rat cecal ligation and puncture model (von Allmen et al., 1990, J. Surg. Res. 48:476–480) and a sheep common bile duct contamination model (Barke et al., 1990, Arch. Surg. 125:437–440).

A rabbit model of barotrauma is known (Ward et al., 1990, Undersea Biomed. Res. 17:51–66).

For animal models of thermal injury, see Bjornson et al., 1986, J. Infect. Dis. 153:1098–1107; Oldham et al., 1988, Surgery 104:272–279; Friedl et al., 1989, Am. J. Pathol. 135:203–217; Demling et al., 1989, Surgery 106:52–59.

An animal model system for rheumatoid arthritis is that consisting of animals of the autoimmune MRL/1 mouse strain (Murphy, E. D. and Roths, J. B., 1978, in *Genetic Control of Autoimmune Disease*, Rose, N. R., et al., eds., Elsevier/North-Holland, New York, pp. 207–219), that develop a spontaneous rheumatoid arthritis-like disease (Hang et al., 1982, J. Exp. Med. 155:1690–1701).

5.9.2. THERAPEUTIC ADMINISTRATION AND COMPOSITIONS

Various delivery systems are known and can be used to administer a Therapeutic of the invention, e.g., encapsulation in liposomes, microparticles, microcapsules, expression by recombinant cells, etc. Other methods of introduction include but are not limited to intradermal, intramuscular, intraperitoneal, intravenous, subcutaneous, intranasal, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local, e.g., direct injection at the inflamed joint of someone suffering from rheumatoid arthritis.

The present invention also provides pharmaceutical compositions. Such compositions comprise a therapeutically effective amount of a Therapeutic, and a pharmaceutically acceptable carrier or excipient. Such a carrier includes but is not limited to saline, buffered saline, dextrose, water, glycerol, ethanol, and combinations thereof. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

6. LYMPHOCYTE ADHESION THROUGH VLA-4: EVIDENCE FOR AN ADDITIONAL α4 INTEGRIN COUNTER-RECEPTOR ON STIMULATED ENDOTHELIUM

We compared the inhibitory effects of anti-VCAM-1 and anti-VLA-4 mAbs on lymphoid cell adhesion to cultured human umbilical vein endothelial cells (HUVEC). The anti-VCAM-1 mAb 4B9 blocked the binding of peripheral blood lymphocytes (PBL) and lymphoid tumor cells to stimulated HUVEC better than the anti-VCAM-1 mAb E1/6. Although the anti-VLA-4 mAb and anti-VCAM-1 mAb 4B9 equally inhibited PBL binding to stimulated HUVEC, mAb 4B9 inhibited the binding of two lymphoid cell lines significantly less than anti-VLA-4 mAb. Combination of 4B9 mAb with function blocking antiserum to human fibronectin, a second known ligand for VLA-4, also failed to inhibit as much as anti-VLA-4 mAb. These findings suggest that adhesion of lymphoid cell lines through VLA-4 or other α4 integrins involves inducible counter-receptor(s) on endothelium distinct from either VCAM-1 or fibronectin. Time course experiments indicate that the fraction of e4 integrin dependent binding that can be blocked by anti-VCAM-1 mAb E1/6 rises and peaks within 2 hr of tumor necrosis factor (TNF) stimulation.

6.1. MATERIALS AND METHODS

6.1.1. CELL CULTURE

HUVEC were purchased from Clonetics Corp. (San Diego, Calif.) and maintained for up to six doublings in M199 media with 20% fetal bovine low endotoxin defined serum (Hyclone), 100 µg/ml bovine endothelial cell growth supplement (Biomedical Technologies, Stoughton, Mass.), 100 µg/ml heparin, 20 mM HEPES, 5 mM glutamine, and 50 µg/ml gentamicin. Tissue culture surfaces were pre-treated with 1 µg/cm$^2$ of human plasma fibronectin in HBSS for 30 min at 37° C. to promote endothelial cell attachment. Human lymphocytic cell lines and SV-40 transformed African green monkey kidney cells (COS) were maintained in complete media (RPMI 1640 with 10% fetal bovine serum, 5 mM glutamine, and 50 µg/ml gentamicin). Peripheral mononuclear cells were obtained by dextran sedimentation and Ficoll-Hypaque (1.077) centrifugation. PBL were enriched by incubating mononuclear cells in complete media on tissue culture plastic twice for 45 min at 37° C.

6.1.2. ANTIBODIES

Mouse anti-human mAb used were TS1/22 (anti-LFA-1) (Sanchez-Madrid et al., 1982, Proc. Natl. Acad. Sci. U.S.A. 79:7489), HP2/1 (anti-VLA-4) (Moser et al., 1989, J. Clin. Invest. 83:444), 4B9 (anti-VCAM-1) (Carlos et al., 1990, Blood 76:965), and E1/6 (anti-VCAM-1) (Rice and Bevilacqua, 1989, Science 246:1303). Antibodies were titrated and used at concentrations 10-fold greater than required to give maximal inhibition of function: 1/250 dilution of TS1/22 ascites, 40 µg/ml of purified HP2/1, 40 µg/ml of purified 4B9, and neat tissue culture supernatant of E1/6. The concentration of E1/6 was both 10-fold higher than the saturation concentration determined from flow cytometry of labeled stimulated HUVEC as well as 10-fold higher than that required to achieve maximum inhibition of Ramos cell adhesion to TNF-stimulated HUVEC. More than 75% of HUVEC stimulated with 25 ng/ml TNF for 24 hr was positive for E1/16. Affinity purified goat antiserum to human fibronectin was from Sigma Chemical Co., St. Louis, Miss.

6.1.3. HUVEC ADHESION ASSAY

PBL or lymphoid tumor cells in complete media/20 mM HEPES were labeled with BCECF-AM and resuspended in complete media/20 mM HEPES. Lymphoid cells were pre-incubated with one or more mAb for 30 min at 37° C., or with medium alone. HUVEC were grown to confluence in 96-well tissue culture plates and incubated for 0 hr to 24 hr at 37° C. with 25 ng/ml of recombinant human TNFe (Genzyme, Boston, Mass.). Prior to testing cell line adhesion, HUVEC monolayers were washed three times with complete media/20 mM HEPES, and to some wells, mAb and/or diluted antiserum were added for 30 min at 37° C., 5% $CO_2$. Lymphoid cells (10$^5$ per well) were overlayed on HUVEC and allowed to settle and adhere for 30 min at 37° C., 5% $CO_2$. To remove non-adherent cells, wells were washed five times by aspirating with a 21g needle and adding 100 µl of complete media/20 mM HEPES. Percent adherence was determined using a fluorescence concentration analyzer (Pandex Laboratories,. Inc., Mundelein, Ill.) by comparing the residual fluorescence concentrations in each well to the input fluorescence concentration.

6.1.4. FIBRONECTIN ADHESION ASSAY

Non-tissue culture 96-well plates were incubated with 5 µg/ml of human plasma fibronectin (New York Blood Center, New York) in 100 mM $NaHCO_3$ for 2 hr at 37° C. and then with 1% heat-treated (30 min, 56° C.) BSA in RPMI 1640 medium for 1 hr at 37° C. Diluted antiserum or mAb were added to some wells for 30 min at 37° C. Lymphoid cells were labeled with BCECF-AM, resuspended in 1% BSA/RPMI, and in some cases, pre-incubated with a mAb for 30 min at 37° C. Labeled lymphoid cells were added at 10$^5$ cells/well and allowed to settle and adhere for 30 min at 37° C., 5% $CO_2$. Unbound cells were removed by washing five times with 1% BSA/RPMI, and percent adherence was determined using a fluorescence concentration analyzer.

6.2. RESULTS

6.2.1. VLA-4-DEPENDENT ADHESION OF LYMPHOCYTIC CELL LINES TO TNF-STIMULATED AND UNSTIMULATED HUVEC

The anti-VLA-4 mAb HP2/1 and the anti-VCAM-1 mAb 4B9 and E1/6 were compared for their abilities to inhibit the adhesion of PBL, Ramos or SKW3 cells to unstimulated HUVEC or to HUVEC stimulated for 24 hr with TNF. To block interactions between LFA-1 and endothelial ICAM-1 or ICAM-2, lymphoid cells were preincubated with the anti-LFA-1 mAb TS1/22. This mAb was confirmed as a functional inhibitor of LFA-1-dependent adhesion by pre-incubating the B lymphocytic cell line JY with mAb TS1/22 and demonstrating a >85% inhibition of JY cells binding to 24 hr TNF-stimulated HUVEC (FIG. 1; Pober and Cotran, 1990, Transplantation 50:537). JY cells express LFA-1 but little if any of the LVA-4 CD29 β subunit (Hemler et al., 1990, Immunological Rev. 114:45).

Pre-incubation with TS1/22 alone inhibited the binding of Ramos or SKW3 cells to TNF-stimulated HUVEC by less than 10% compared to pre-incubation with medium alone; TS1/22 inhibited PBL binding by less than 20% compared to medium alone (FIG. 2A–2C). When PBL, Ramos or SKW3 cells were pre-incubated with the anti-VLA-4 mAb HP2/1 in addition to TS1/22, binding to TNF-stimulated HUVEC was significantly inhibited compared to binding following incubation with medium alone (FIG. 2). Adhesion of PBL to TNF-stimulated HUVEC was blocked by 55%, Ramos cells by 85%, and SKW3 cells by 60%.

Pre-incubation of TNF-stimulated HUVEC with the anti-VCAM-1 mAb 4B9 (in addition to lymphoid cell pre-incubation with TS1/22) blocked binding of PBL equally as well as pre-incubation with HP2/1 and TS1/22 (FIG. 2A). In contrast, the anti-VCAM-1 mAb E1/6 blocked binding of PBL to TNF-stimulated HUVEC by only a fraction of that observed following preincubation with HP2/1 and TS1/22, or 4B9 and TS1/22. For Ramos or SKW3 cells (FIG. 2B–C), pre-incubation of TNF-stimulated HUVEC with either 4B9 or E1/6 (in addition to cell line pre-incubation with TS1/22) failed to block binding as well as HP2/1 and TS1/22. For each cell line, however, inhibition with 4B9 was significantly greater than that with E1/6.

For each cell type tested, adhesion to unstimulated HUVEC was substantially less than adhesion to TNF-stimulated HUVEC (FIG. 2A–2C). Preincubation with TS1/22 alone modestly but significantly inhibited adhesion of PBL and SKW3 cells to unstimulated HUVEC; TS1/22 did not inhibit binding of Ramos cells to unstimulated HUVEC. When PBL, Ramos or SKW3 cells were pre-incubated with HP2/1 in addition to TS1/22, only slight further inhibition in binding was observed, indicating that VLA-4 counter-receptor(s) on endothelium are cytokine inducible. Basal cell line adhesion to unstimulated HUVEC was not affected by additionally pre-incubating HUVEC with anti-VCAM-1 mAb 4B9 or E1/6 (FIG. 2A–2C).

6.2.2. A LIGAND ON STIMULATED ENDOTHELIUM DISTINCT FROM VCAM-1 AND FIBRONECTIN

The two cell lines we examined, but not PBL, bound to stimulated endothelium through a pathway that was blocked by mAb to the VLA-4 α subunit but not by 4B9 mAb to VCAM-1. These mAb completely blocked binding of the same cells to COS cells expressing VCAM-1. Because VLA-4 can bind to an alternatively spliced form of fibronectin (Guan and Hynes., 1990, Cell 60:53; Wayner et al., 1989, J. Cell Biol. 109:1321), we assessed whether anti-fibronectin antiserum could block cell line binding to TNF-stimulated HUVEC. To demonstrate anti-fibronectin antiserum as an inhibitor of lymphocyte-fibronectin adhesion, we determined the binding of Ramos and SKW3 cells to purified plasma fibronectin absorbed onto plastic microtiter plates at 5 μg/ml. For both cell lines, binding to purified fibronectin was completely inhibited by pre-incubation of the plates with antiserum to human fibronectin (FIG. 3A). Cell line pre-incubation with the anti-VLA-4 mAb HP2/1 also completely blocked binding to fibronectin whereas preincubation with the anti-LFA-1 mAb TS1/22 had no effect. Cell line binding to bovine serum albumin was minimal (FIG. 3A). Neither Ramos nor SKW3 express VLA-5, as determined by flow cytometric analysis (data not shown). This result therefore confirms previous reports of VLA-4- dependent/VLA-5-independent adhesion of lymphocytes to fibronectin (Guan and Hynes, 1990, Cell 60:53; Wayner et al., 1989, J. Cell Biol. 109:1321).

Pre-incubation of 24 hr TNF-stimulated HUVEC with anti-fibronectin antiserum (in addition to cell line pre-incubation with the anti-LFA-1 mAb TS1/22) inhibited Ramos cell adhesion by <20% and SXW3 cell adhesion by <12% (FIG. 3B). When anti-fibronectin antiserum was used in combination with anti-VCAM-1 mAb 4B9 or E1/6, no or only a moderate additive effect on the inhibition of adhesion to TNF-stimulated HUVEC was observed (additional inhibition <8%) (FIG. 3B). Inhibition remained substantially less than that obtained with VLA-4 mAb. These results suggest that cell lines express an integrin containing the VLA-4 α subunit that can recognize a ligand on stimulated endothelium that is distinct from VCAM-1 and fibronectin.

6.2.3. INDUCTION OF E1/6-DEPENDENT/VLA-4-DEPENDENT RAMOS CELL ADHESION TO TNF-STIMULATED HUVEC

To determine the induction of E1/6-dependent adhesion of lymphoid cells to HUVEC, we assessed Ramos cell binding to HUVEC following 0 hr, 2 hr, 3.5 hr, or 7 hr of TNF stimulation. HUVEC used for any one experiment were from a single umbilical cord. VLA-4-dependent adhesion was calculated as the percentage of Ramos cell binding that was blocked by anti-VLA-4 mAb HP2/1 in the presence of anti-LFA-1 mAb TS1/22. For five experiments, VLA-4-dependent adhesion increased as the time of TNF stimulation increased (FIG. 4, Table 1), consistent with the cytokine inducibility of VLA-4 counter-receptor(s) on endothelium. There was no significant VLA-4-dependent adhesion to unstimulated HUVEC.

TABLE 1

| mAb | % cells binding TNF stimulation | | | |
|---|---|---|---|---|
| | 0 hr | 2 hr | 3.5 hr | 7 hr |
| TS1/22 | 8.2 ± 1.3 | 17.7 ± 2.3 | 22.7 ± 5.6 | 26.5 ± 4.9 |
| TS1/22 + HP2/1 | 7.1 ± 2.3 | 6.4 ± 1.8 | 6.9 ± 2.3 | 6.0 ± 1.7 |
| TS1/22 + E1/6 | 9.5 ± 3.0 | 10.2 ± 1.8 | 16.2 ± 4.0 | 23.8 ± 3.2 |

VLA-4-dependent adhesion that could be blocked by E1/6 in the presence of anti-LFA-1 mAb TS1/22 was characterized as E1/6-dependent. Results from five experiments showed that after 2 hr of TNF stimulation, the majority of VLA-4-dependent binding of Ramos cells was E1/6-dependent, but after 7 hr of stimulation, the majority of VLA-4-dependent adhesion was not blocked by E1/6 (FIG. 4).

6.3. DISCUSSION

The integrin VLA-4 mediates lymphocyte adhesion to stimulated endothelium by binding to VCAM-1, a member of the immunoglobulin superfamily whose expression is induced on endothelium by proinflammatory cytokines (Elices et al., 1990,, Cell 60:577; Osborn et al., 1989, Cell 59:1203; Rice and Bevilacqua, 1989, Science 246:1303). At least two different precursors for VCAM-1 can be generated from the human VCAM-1 gene as a result of alternative mRNA splicing (Cybulsky et al., 1991, Proc. Natl, Acad. Sci. U.S.A. 88:7859). The resulting proteins correspond to a six Ig domain form of VCAM-1 (VCAM-6D) and a seven Ig domain form (VCAM-7D).

Using the HUVEC system, we directly compared the inhibitory effects of the anti-VLA-4 mAb HP2/1 and the anti-VCAM-1 mAb 4B9 in order to determine whether there might exist VLA-4 counter-receptors distinct from VCAM-1. Here, we chose mAb HP2/1 to VLA-4 α and 4B9 to VCAM-1 for comparison because either mAb used alone completely blocks lymphoid cell binding to either form of VCAM-1 (data not shown). Also, it has been shown that mAb HP2/1 completely blocks two other adhesive functions of VLA-4; namely, interactions with fibronectin and lymphocyte homotypic aggregation (Pulido et al., 1991, J. Biol Chem. 266:10241). In experiments with PBL, mAb HP2/1 and 4B9 blocked adhesion to stimulated HUVEC equally well, suggesting no use of alternative VLA-4 counter-receptors; however, for the two cell lines tested, mAb HP2/1 blocked adhesion to stimulated HUVEC significantly better than mAb 4B9. When function blocking antisera to human fibronectin was used in combination with mAb 4B9, inhibition was still significantly less than that observed with mAb HP2/1. These results provide evidence for the existence of counter-receptor(s) for an α4 integrin that are inducible on the surface of endothelium and are distinct from VCAM-6D, VCAM-7D, and fibronectin. Our functional evidence for a pathway of adhesion of T cell lines to stimulated endothelium that is blocked by VLA-4 α subunit mAb but not VCAM-1 mAb is particularly strong because of our demonstration that these mAb equally block adhesion of the same T cell lines to VCAM-1 cDNA-transfected COS cells, and adhesion of PBL to stimulated endothelium.

It is not known why the two lymphocytic cell lines were found to bind novel α4 integrin counter-receptor(s) but resting PBL were not. There may be differences in the activation of αβ1, by resting PBL vs. lymphoid tumor cells that confer variations in function, such as proteolytic cleavage of the α4 subunit or cellular signals that regulate α4β1 avidity (Hemler, 1990, Annu. Rev. Immunol. 8:365; Hemler et al., 1990, Immunological Rev. 114:45; Shimizu et al., 1990, Nature 345:250; Shimizu et al., 1991, J. Cell Biol. 113:1203). Alternatively, the α4 subunit may associate with distinct β subunits, such as β7 (Turunen et al., 1990, J. Immunol. 145:4192; Erle et al., 1991, J. Biol. Chem. 266:11009), and function with a unique ligand specificity. Curiously, mRNA for β7 has been easily detected in some lymphocytic cell lines but not in resting peripheral T cells (Erle et al., 1991, J. Biol. Chem. 266:11009).

7. FUNCTIONAL CLONING OF THE VLA-4 RECEPTOR

7.1. PANNING METHOD

Purified VLA-4 is coated on plastic, and a modified version of the procedure of Aruffo and Seed (1987, Proc. Natl. Acad. Sci. USA 84:3365–3369) for selecting cDNAs by expression in COS cells is used, as modified by Staunton et al. (1989, Nature 339:61–64) for the cloning of ICAM-2, as detailed below.

VLA-4 is purified from tonsil cell lysates by immunoaffinity chromatography on anti-VLA-4 mAb Sepharose, and eluted at basic pH in the presence of 2 mM $MgCl_2$ and 1% octylglucoside. Alternatively, purified VLA-4 is obtained by recombinant methods by expression from cells transfected with a DNA clone encoding VLA-4 (Elices et al., 1990, Cell 60:577). VLA-4 (10 µg per 200 µl per 6-cm plate) is bound to bacteriological Petri dishes by diluting octylglucoside to 0.1% in PBS with 2 mM $MgCl_2$ and overnight incubation at 4° C. Plates are blocked with 1% BSA and stored in PBS/2 mM $MgCl_2$/0.2% BSA/0.025% azide/50 µg ml$^{-1}$ gentamycin. Synthesis of a cDNA library from lipopolysaccharide-stimulated umbilical vein endothelial cells is as described previously (Staunton et al., 1988, Cell 52:925–933). After second-strand synthesis, the cDNA is ligated to BstXI adaptors (Seed and Aruffo, 1987, Proc. Natl. Acad. Sci. USA 84:3365–3369), and cDNAs longer than 600 bp are selected by low-melting point agarose gel electrophoresis. The cDNA is then preferably ligated to a plasmid vector such as CDM8 (Seed, 1987, Nature 329:840–842), that replicates in certain prokaryotic as well as certain eukaryotic cells and provides for expression of recombinant proteins in certain eukaroytic cells. The vectors are then introduced into *E. coli* host MC1061/P3 and plated to obtain 5×10$^5$ colonies. The colonies are suspended in LB medium, pooled and plasmid prepared by standard alkali-lysis method (Sambrook et al., 1989, in *Molecular Cloning, A Laboratory Manual*, 2d ed., Cold Spring Harbor Laboratory, New York). Ten 10-cm plates of COS cells at 50% confluency are transfected with 10 µg per plate of the plasmid cDNA library using DEAE-dextran (Kingston, 1987, in *Current Protocols in Molecular Biology*, Greene Publishing Assocs., pp. 911–996). COS cells three days after transfection are suspended by treatment with 0.025% trypsin/1 mM EDTA/HBSS (Gibco) and with 5 µg/ml of anti-VCAM-1 monoclonal antibody 4B9 (Carlos et al., 1990, Blood 76:965) and preferably also with anti-fibronectin antiserum, and panned (Seed and Aruffo, 1987, Proc. Natl. Acad. Sci. USA 84:3365–3369) on VLA-4 coated plates. The cell suspension is incubated in the VLA-4 coated plates at 25° C. for 1 hour. The transfected COS cells are incubated in the VLA-4 coated dishes with anti-VCAM-1 and preferably also with anti-fibronectin antibody present to prevent isolation of VCAM-1 or fibronectin cDNA. Nonadherent cells are removed by gentle rocking and three washes with buffer. Adherent cells are eluted by addition of 10 mM EDTA. Plasmid is recovered from the adherent population of COS cells in Hirt supernatants. The *E. coli* strain MC1061/P3 is transformed with the plasmid, and colonies on plates are suspended in LB medium, pooled, and plasmid is prepared by the alkal-ilysis method. Selection of VLA-4-adherent transfected COS cells and plasmid recovery is repeated twice. Pooled colonies obtained after the third cycle are grown to saturation in 100 ml LB medium with 18 µg/ml tetracycline and 20 µg/ml ampicillin. Plasmid is prepared and fractionated by 1% low-melting point agarose gel electrophoresis, and MC1061/P3 is transformed separately with plasmid from different size fractions. Individual plasmids from the fraction with greatest activity in promoting adhesion to VLA-4 of COS cells transfected with such plasmids are examined for uniqueness by restriction enzyme digestion and re-tested in the COS cell adherence assay.

7.2. ROSETTE METHOD

In another embodiment, for functional cloning of the Receptor, COS cells transfected with a plasmid cDNA library synthesized from stimulated human umbilical vein endothelial cell mRNA are cultured on a plastics surface of a tissue culture dish. Preferably, the cDNA library is in a plasmid vector (e.g., CDM8; Seed, 1987, Nature 329:840–842) that replicates in certain prokaryotic as well as certain eukaryotic cells and provides for expression of recombinant proteins in certain eukaroytic cells. The COS cells are incubated with a medium comprising (i) cells of a VLA-4 (or other α4 integrin)- expressing lymphoid cell line, and (ii) an anti-VCAM-1 mAb that blocks binding of VLA-4 (or the other α4 integrin) to VCAM-1. In addition, the incubation is preferably also in the presence of an anti-fibronectin antiserum that blocks binding of fibronectin to VLA-4 (or the other α4 integrin). If the lymphoid cell line expresses LFA-1 (e.g., Ramos, SKW3) the incubation is preferably also in the presence of an LFA-1 mAb that blocks binding of LFA-1 to its counter-receptors ICAM-1 and ICAM-2. The incubation is carried out for a time period sufficient to allow binding of lymphoid cells to a transfected COS cell. A COS cell to which a "rosette" of ten or more lymphoid cells are bound is isolated. This is accomplished by using a plastic cloning cylinder preferably less than 5 mm in diameter and about 1 cm tall, with vacuum grease at its edge to form a seal, to surround the COS cell on the plastic surface. A trypsin-EDTA solution is poured into the plastic cylinder, and allowed to sit for five minutes at room temperature, in order to elute the COS cell from the plastic. The cell solution is then removed to a microfuge tube, and plasmid cDNA is purified from the eluted cell(s) by known methods. Since sometimes more than a single COS cell is thus isolated, and since a single COS cell can contain more than one cDNA clone, preferably, additional procedures are then used to isolate a single clone: The purified cDNA is used to transform competent *E. coli*, followed by purification of cDNA from individual colonies of transformed *E. coli*. Samples containing each individual cDNA clone are used to transfect COS cells which are then cultured on plastic and incubated with a medium comprising cells of a lymphoid cell line that express VLA-4 (or other α4 integrin) in the presence of an anti-VCAM-1 mAb such as described above, and preferably also in the presence of an anti-fibronectin antiserum as described above. If the lymphoid cells express LFA-1, the incubation is preferably done also in the presence of an anti-LFA-1 mAb that blocks binding of LFA-1 to ICAM-1 and ICAM-2. The incubation is carried out for a period of time sufficient to allow binding of a lymphoid cell to a transfected COS cell. The cDNA clone which gave rise to a transfected COS cell thus bound is identified as the Receptor cDNA clone.

7.3. SUBPOOL SELECTION

In this embodiment, for functional cloning of a Receptor cDNA, a plasmid cDNA library is used, synthesized from stimulated human umbilical vein endothelial cell mRNA, preferably in plasmid CDM8. A plasmid vector such as CDM8 (Seed, 1987, Nature 329:840–842) is preferably used since it replicates in certain prokaryotic as well as certain eukaryotic cells and provides for expression of recombinant proteins in certain eukaryotic cells. The cDNA library in *E. coli* is plated out. Samples of subpools (portions) of the library (totalling about 300,000 colonies) consisting of cDNA from less than 1,000 colonies is used to transfect COS cells, which are then cultured on plastic and incubated with a medium comprising (i) cells of a VLA-4 (or other α4 integrin)-expressing lymphoid cell line, and (ii) an anti-VCAM-1 mAb that blocks binding of VLA-4 (or the other α4 integrin) to VCAM-1. In addition, the incubation is preferably also in the presence of an anti-fibronectin antiserum that blocks binding of fibronectin to VLA-4 (or the other α4 integrin). If the lymphoid cell line expresses LFA-1 (e.g., Ramos, SKW3), the incubation is preferably also in the presence of an anti-LFA-1 mAb that blocks binding of LFA-1 to its counter-receptors ICAM-1 and ICAM-2. The incubation is carried out for a time period sufficient to allow binding of lymphoid cells to a transfected COS cell. A subpool of the cDNA library is identified that, upon the foregoing transfection and analysis, yields significantly increased binding of the lymphoid cells to the transfected COS cell, relative to the binding of lymphoid cells to COS cells transfected with CDM8 vector alone (without a cDNA insert). From the original subpool thus identified, are obtained and plated further subpool plasmid cDNA samples, each further subpool consisting of less than 40 colonies. A sample from this further subpool is transfected into COS cells and again assayed as described above. The further subpool is identified that, upon the foregoing transfection and analysis, yields relatively high level binding of the lymphoid cells. Single plasmid cDNAs are then obtained from this identified further subpool on the original plate, transfected into COS cells, and again assayed as described above.. The cDNA molecule is isolated that, upon transfection and assay as described above, yields relatively high level binding of the lymphoid cells.

8. PRODUCTION OF ANTIBODY AND ISOLATION OF THE α4 RECEPTOR BY ANTIBODY BINDING

A monoclonal antibody is raised, against the Receptor of the invention, that, in combination with blocking mAb to VCAM-1 and with blocking antiserum to fibronectin, can completely inhibit binding of lymphoid cell lines to cultured human umbilical vein endothelial cells (HUVEC).

Cell culture is carried out as described in Section 6.1.1, supra.

Stimulated HUVEC are used to immunize 3–12-wk-old BALB/c female mice (Charles River Laboratories, Wilmington, Mass.). Immunizations ($10^5$–$10^6$ cells per intraperitoneal immunization) are given three times at 3-wk intervals. Three days before fusion of antibody-secreting cells with the murine myeloma P3X63Ag8.653, the mice are injected both intraperitoneally and intravenously with $5\times10^5$ HUVEC cells. The protocol for fusion and subsequent maintenance of hybridomas is as described previously (Galfre and Milstein, 1981, Meth. Enzymol. 73:3). Approximately 1,000 hybridomas are screened for the ability to inhibit stimulated HUVEC binding to Ramos or SKW3 cells in the presence of anti-LFA-1 mAb and anti-VCAM-1 mAb 4B9 (Carlos et al., 1990, Blood 76:965) and preferably also in the presence of an anti-fibronectin antiserum. An antibody with such ability is cloned three times by limiting dilution. The antibody is once again screened for the ability, in combination with mAb 4B9 and anti-fibronectin antiserum, to completely inhibit SKW3 or Ramos binding to stimulated HUVEC. The antibody can be isotyped by ELISA using affinity-purified antibodies to mouse immunoglobulins (Zymed Immunochemicals, San Francisco, Calif.).

Alternatively, neutralizing antibodies to the Receptor can be identified by an assay such as those described in Section 5.7.1 supra.

To purify the α4 Receptor, the mAb isolated above is used in immunoaffinity chromatography by known methods to isolate the Receptor, or in immunoprecipitation assays.

For immunoprecipitation of the α4 Receptor, HUVEC are surface labeled with $^{125}$I as described using Iodogen (Pierce Chemical Co., Rockford, IL) (Kishimoto et al., 1989, J. Biol. Chem. 264:3588). Triton X-100 (1%) lysates are cleared with bovine IgG-coupled-Sepharose and then incubated with the mAb-bound Sepharose for 2 h. Beads are washed and heated at 100° C. in sample buffer containing 50 mM Tris, 1% SDS, and 1% 2-mercaptoethanol or 20 mM iodoacetamide. Samples are subjected to sodium dodecyl sulfate 7% polyacrylamide gel electrophoresis (Laemmli, 1970, Nature 227:680) and autoradiography with enhancing screens.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method for isolating a cDNA molecule encoding a receptor for an α4 integrin, comprising the following steps in the order stated:

(a) incubating a solid phase surface containing purified α4 integrin molecules with a medium comprising (i) recombinant cells, said recombinant cells containing and expressing the proteins encoded by a plurality of cDNA molecules synthesized from stimulated endothelial cell mRNA, and (ii) a monoclonal antibody to VCAM-1 that blocks binding of the α4 integrin to VCAM-1, for a time period sufficient to allow binding of a recombinant cell to the solid phase surface;

(b) removing the recombinant cells that are not bound to the solid phase surface;

(c) eluting a bound cell from the solid phase surface; and (d) isolating the cDNA molecule present in the eluted cell.

2. The method according to claim 1 in which the medium of step (a) further comprises an antiserum to fibronectin that blocks binding of the α4 integrin to fibronectin.

3. A method for isolating a cDNA molecule encoding a receptor for an α4 integrin, comprising the following steps in the order stated:

(a) incubating recombinant cells cultured on a solid phase surface with a medium comprising (i) cells of a lymphoid cell line which expresses an α4 integrin, and (ii) a monoclonal antibody to VCAM-1 that blocks binding of the α4 integrin to VCAM-1, for a time period sufficient to allow binding of lymphoid cells to a recombinant cell, said recombinant cells containing and expressing the proteins encoded by a plurality of cDNA molecules synthesized from stimulated endothelial cell mRNA;

(b) recovering at least one recombinant cell to which at least ten lymphoid cells are bound;

(c) isolating the one or more cDNA molecules present in the recovered cell;

(d) introducing each isolated cDNA molecule from step (c) individually into host cells which can express the cDNA molecule;

(e) incubating said host cells cultured on a solid phase surface with a medium comprising (i) cells of a lymphoid cell line which expresses an α4 integrin, and (ii) a monoclonal antibody to VCAM-1 that blocks binding of the α4 integrin to VCAM-1, for a time period sufficient to allow binding of lymphoid cells to a host cell; and (f) isolating the cDNA molecule of step (c) that is contained in a host cell of step (e) to which a lymphoid cell is bound.

4. The method according to claim 3 in which the medium of steps (a) and (e) further comprises (i) an antiserum to fibronectin that blocks binding of the α4 integrin to fibronectin, and (ii) an anti-LFA-1 monoclonal antibody that blocks binding of LFA-1 to ICAM-1 and ICAM-2.

5. A method for isolating a cDNA molecule encoding a receptor for an α4 integrin, comprising the following steps in the order stated:

(a) incubating recombinant cells cultured on a solid phase surface with a medium comprising (i) cells of a lymphoid cell line which expresses an α4 integrin, and (ii) a monoclonal antibody to VCAM-1 that blocks binding of the α4 integrin to VCAM-1, for a time period sufficient to allow binding of lymphoid cells to a recombinant cell, said recombinant cells containing and expressing plasmids comprising cDNA molecules present in a first group of less than 1,000 cDNA molecules from a library synthesized from stimulated endothelial cell mRNA;

(b) identifying said first group that results in increased binding of the lymphoid cells to a recombinant cell in step (a), relative to the binding of the lymphoid cells to a recombinant cell containing the plasmid without a cDNA molecule;

(c) dividing the identified first group into a second group of less than 40 cDNA molecules;

(d) introducing cDNA molecules from the second group into host cells which can express the cDNA molecules;

(e) incubating said host cells of step (d) cultured on a solid phase surface with a medium comprising (i) cells of a lymphoid cell line which expresses an α4 integrin; and (ii) a monoclonal antibody to VCAM-1 that blocks binding of the α4 integrin to VCAM-1, for a time period sufficient to allow binding of lymphoid cells to a host cell;

(f) identifying said second group that results in increased binding of the lymphoid cells to a host cell in step (e), relative to the binding of the lymphoid cells to a host cell containing the plasmid without a cDNA molecule;

(g) dividing the identified second group into a third group of single plasmid cDNA molecules;

(h) introducing cDNA molecules from the third group into host cells which can express the cDNA molecules;

(i) incubating said host cells of step (h) cultured on a solid phase surface with a medium comprising (i) cells of a lymphoid cell line which expresses an α4 integrin, and (ii) a monoclonal antibody to VCAM-1 that blocks binding of the α4 integrin to VCAM-1, for a time period sufficient to allow binding of lymphoid cells to a host cell; and (j) isolating the cDNA molecule from the third group that results in increased binding of the lymphoid cells to a host cell in step (i), relative to the binding of the lymphoid cells to a host cell containing the plasmid without a cDNA molecule.

6. The method according to claim 5 in which the medium of steps (a), (e) and (i) further comprises an antiserum to fibronectin that blocks binding of the α4 integrin to fibronectin, and an anti-LFA-1 monoclonal antibody that blocks binding of LFA-1 to ICAM-1 and ICAM-2.

7. The method according to claim 6 which further comprises before step (c) the step of replicating the plasmids from the identified first group in *E. coli;* and which further comprises before step (g) the step of replicating the plasmids from the identified second group in *E. coli.*

8. A method for isolating a cDNA molecule encoding a receptor for VLA-4 or for the VLA-4 α4 subunit, comprising the following steps in the order stated:

(a) incubating a plastic surface of a dish, said surface coated with purified VLA-4, with a medium comprising (i) COS cells transfected with an expression plasmid cDNA library synthesized from stimulated human umbilical vein endothelial cell mRNA, and (ii) a monoclonal antibody to VCAM-1 that blocks binding of VLA-4 to VCAM-1, for a time period sufficient to allow binding of a transfected cell to the plastic surface;

(b) removing the transfected COS cells that are not bound to the surface;

(c) washing the surface;

(d) eluting a bound cell from the surface; and (e) isolating a cDNA molecule present in the eluted cell.

9. The method according to claim 8 in which the medium of step (a) further comprises an antiserum to fibronectin that blocks binding of VLA-4 to fibronectin.

10. A method for isolating a cDNA molecule encoding a receptor for an α4 integrin, comprising the following steps in the order stated:

(a) incubating a solid phase surface containing purified α4 integrin molecules with a medium comprising (i) recombinant cells, said recombinant cells containing and expressing the proteins encoded by a plurality of cDNA molecules synthesized from stimulated endothelial cell mRNA, (ii) a monoclonal antibody to VCAM-1 that blocks binding of the α4 integrin to VCAM-1, (iii) an antiserum to fibronectin that blocks binding of the α4 integrin to fibronectin, and (iv) an anti-LFA-1 monoclonal antibody that blocks binding of LFA-1 to ICAM-1 and ICAM-2, for a time period sufficient to allow binding of a recombinant cell to the solid phase surface;

(b) removing the recombinant cells that are not bound to the solid phase surface;

(c) eluting one or more bound cells from the solid phase surface;

(d) recovering the one or more cDNA molecules present in the eluted one or more cells;

(e) replicating the recovered cDNA molecules in *E. coli;*

(f) introducing the cDNA molecules into recombinant cells capable of expressing the protein encoded by said cDNA molecules; and (g) repeating steps (a) through (d) wherein said recombinant cells are the recombinant cells of step (f), until one cDNA molecule is recovered in step (d).

* * * * *